United States Patent

Hickle et al.

Patent Number: 5,676,133
Date of Patent: Oct. 14, 1997

[54] EXPIRATORY SCAVENGING METHOD AND APPARATUS AND OXYGEN CONTROL SYSTEM FOR POST ANESTHESIA CARE PATIENTS

[75] Inventors: Randall S. Hickle; Richard B. Adams, both of Lubbock, Tex.; William A. Pesa, Wooster, Ohio; James L. Earsley, Lubbock, Tex.; Richard A. Liles, Lubbock, Tex.; James C. De Villiers, Lubbock, Tex.

[73] Assignee: Apotheus Laboratories, Inc., Lubbock, Tex.

[21] Appl. No.: 658,199

[22] Filed: Jun. 4, 1996

[51] Int. Cl.⁶ .................................................. A61M 16/00
[52] U.S. Cl. .................... 128/205.12; 128/202.27; 128/204.18; 128/205.24; 128/205.25; 128/206.21; 128/206.22; 128/206.24; 128/206.25; 128/910
[58] Field of Search ................ 128/200.14, 200.26, 128/204.18, 204.24, 204.27, 204.28, 205.12, 205.14, 205.25, 206.21, 206.24, 206.25, 206.26, 206.28, 206.29, 205.15, 909, 910, 202.27, 206.22, 205.27, 205.24

[56] References Cited

U.S. PATENT DOCUMENTS

| | | | |
|---|---|---|---|
| 2,254,854 | 9/1941 | O'Connell | 128/206.25 |
| 2,837,090 | 6/1958 | Bloom et al. | 128/206.24 |
| 2,880,719 | 4/1959 | Andreasen | 128/205.15 |
| 2,931,356 | 4/1960 | Schwarz | 128/206.24 |
| 3,291,122 | 12/1966 | Engström et al. | 128/205.15 |
| 3,467,092 | 9/1969 | Bird et al. | 128/205.15 |
| 3,664,335 | 5/1972 | Boucher et al. | 128/206.19 |
| 3,850,168 | 11/1974 | Ferguson et al. | 128/206.27 |
| 3,973,564 | 8/1976 | Carden | 128/205.14 |
| 4,192,785 | 3/1980 | Chen et al. | 128/206.25 |
| 4,196,727 | 4/1980 | Verkaart et al. | 128/206.24 |
| 4,337,767 | 7/1982 | Yahata | 128/206.28 |
| 4,382,440 | 5/1983 | Kapp et al. | 128/205.28 |
| 4,506,665 | 3/1985 | Andrews et al. | 128/205.25 |
| 4,580,556 | 4/1986 | Kondur | 128/206.29 |
| 4,653,493 | 3/1987 | Hoppough | 128/202.22 |
| 4,750,482 | 6/1988 | Sieverding | 604/317 |
| 4,794,921 | 1/1989 | Lindkvist | 128/206.28 |
| 4,807,617 | 2/1989 | Nesti | 128/206.28 |
| 4,873,970 | 10/1989 | Freidank et al. | 128/205.27 |
| 4,966,140 | 10/1990 | Herzberg | 128/206.25 |
| 5,143,061 | 9/1992 | Kaimer | 128/206.25 |
| 5,322,061 | 6/1994 | Brunson | 128/206.13 |
| 5,348,000 | 9/1994 | Teves | 128/204.18 |
| 5,368,021 | 11/1994 | Beard et al. | 128/205.14 |
| 5,400,779 | 3/1995 | De Resende | 128/205.24 |
| 5,404,873 | 4/1995 | Leagre et al. | 128/205.25 |
| 5,406,943 | 4/1995 | Hubbard et al. | 128/206.23 |
| 5,507,280 | 4/1996 | Henkin et al. | 128/205.15 |
| 5,529,056 | 6/1996 | Brunson et al. | 128/206.25 |
| 5,540,223 | 7/1996 | Starr et al. | 128/205.25 |

FOREIGN PATENT DOCUMENTS

| | | | |
|---|---|---|---|
| 0601708 | 6/1994 | European Pat. Off. | 128/200.14 |
| 2537695 | 6/1984 | France | 128/206.21 |
| 2072516 | 3/1980 | United Kingdom | 128/206.21 |
| 1588442 | 4/1981 | United Kingdom | 628/18.02 |

*Primary Examiner*—Vincent Millin
*Assistant Examiner*—Virendra Srivastava
*Attorney, Agent, or Firm*—Dorsey L. Baker

[57] ABSTRACT

An apparatus and method for preventing contamination of the Post Anesthesia Care Unit of A Hospital by the use of a mask sealed to the patient's face and connected by a ventilator circuit to an airator that pulls a vacuum to exhaust the patient's expirations to the outside atmosphere. The disclosure also includes a "oxyvent" which is a tube adapted to be attached to an oxygen tank and to a patient to provide a higher oxygen ratio to the patient and to provide forced ventilation to a patient who has difficulty ventilating.

40 Claims, 11 Drawing Sheets

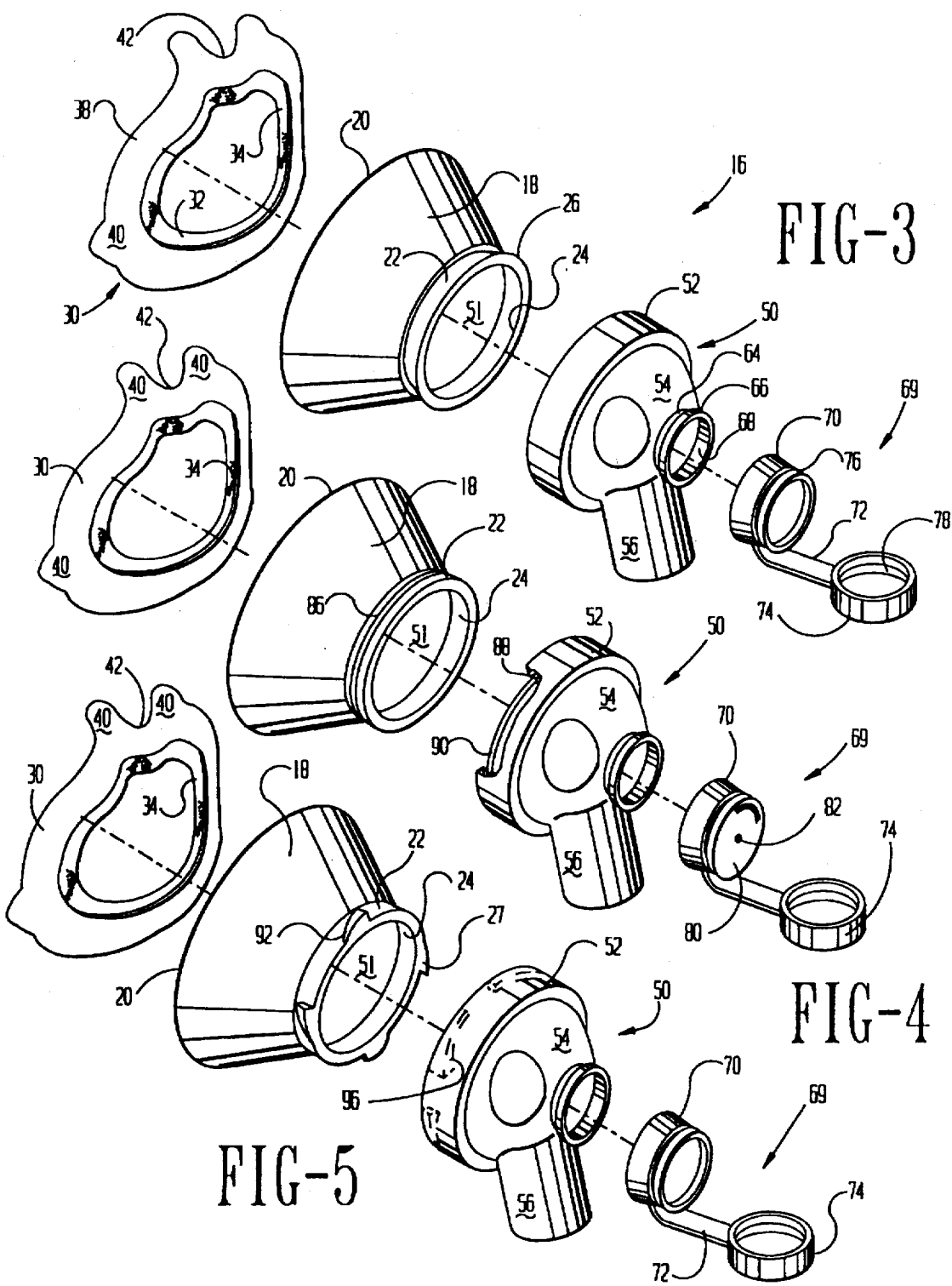

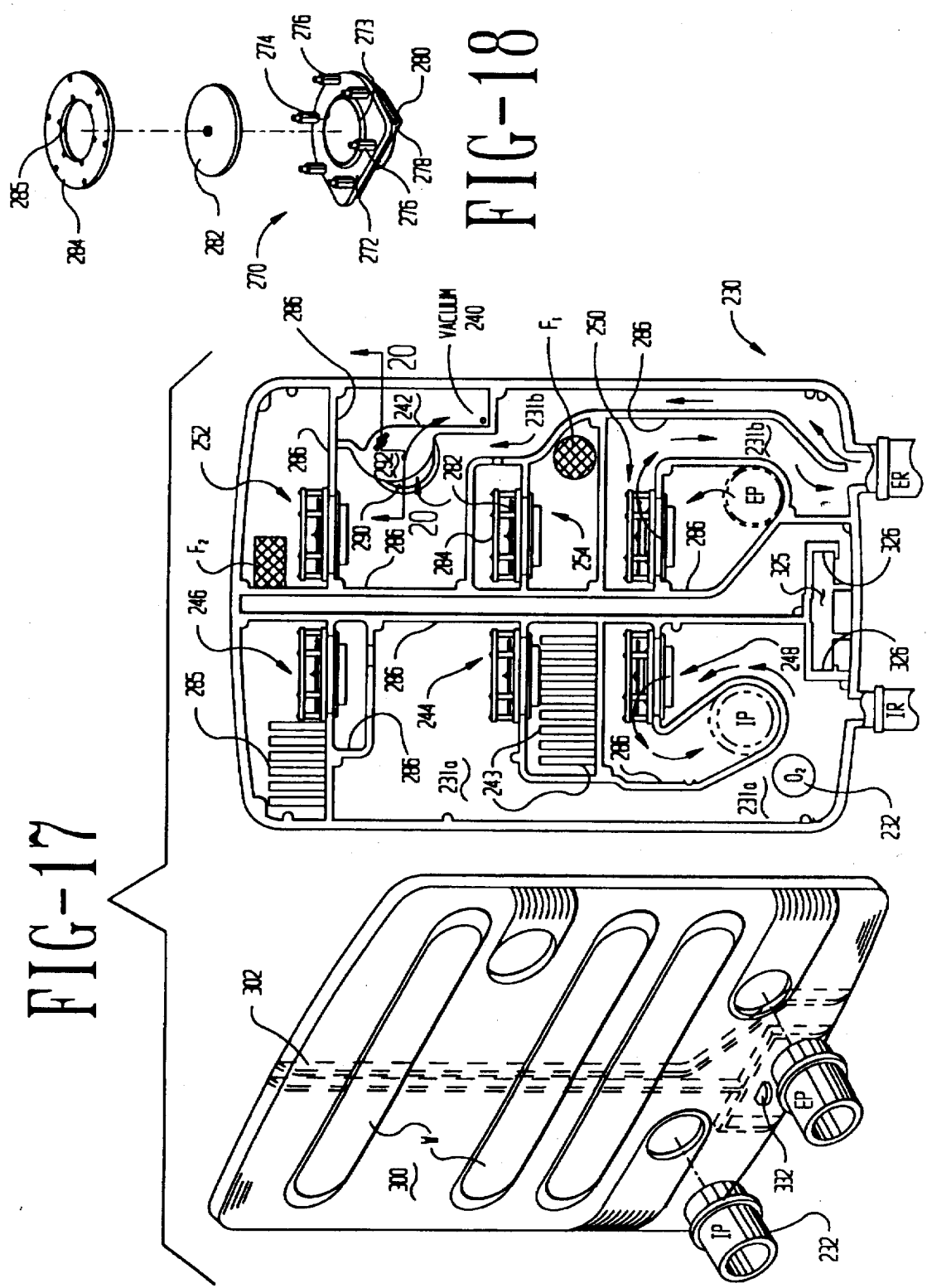

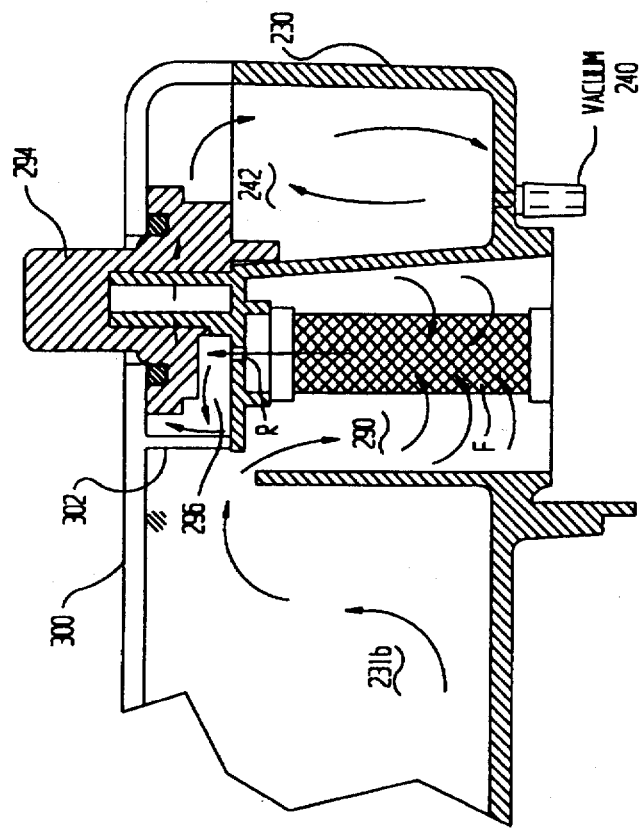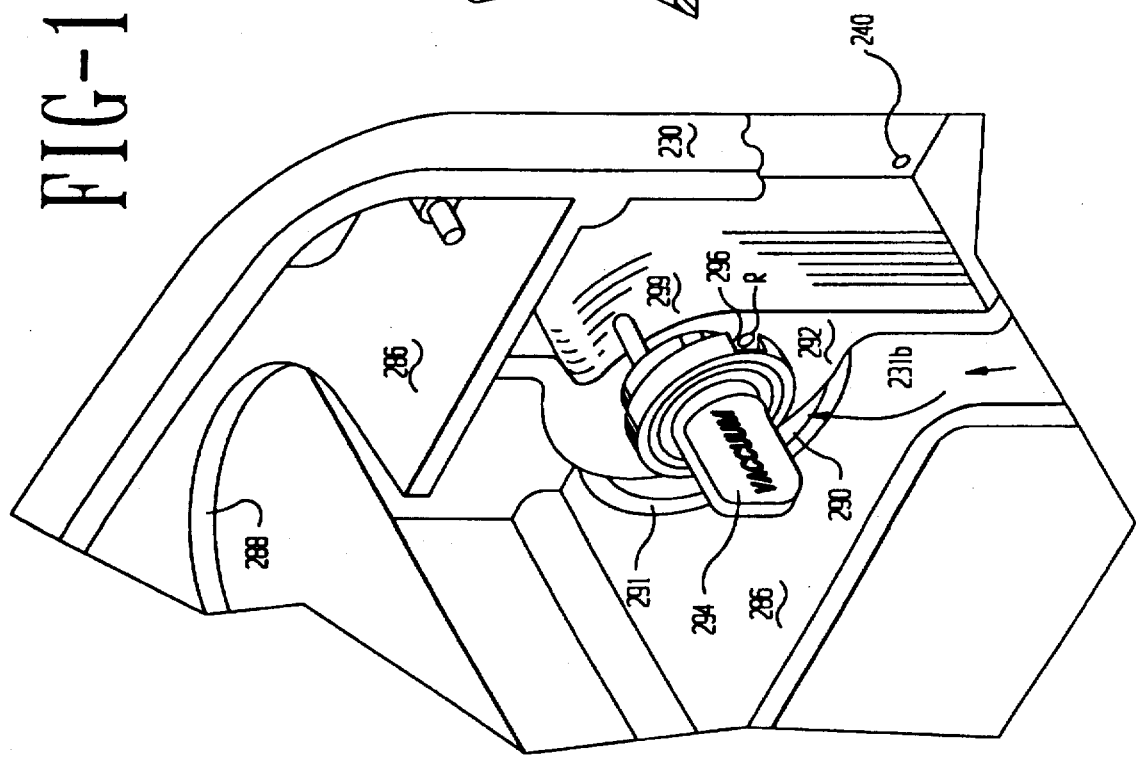

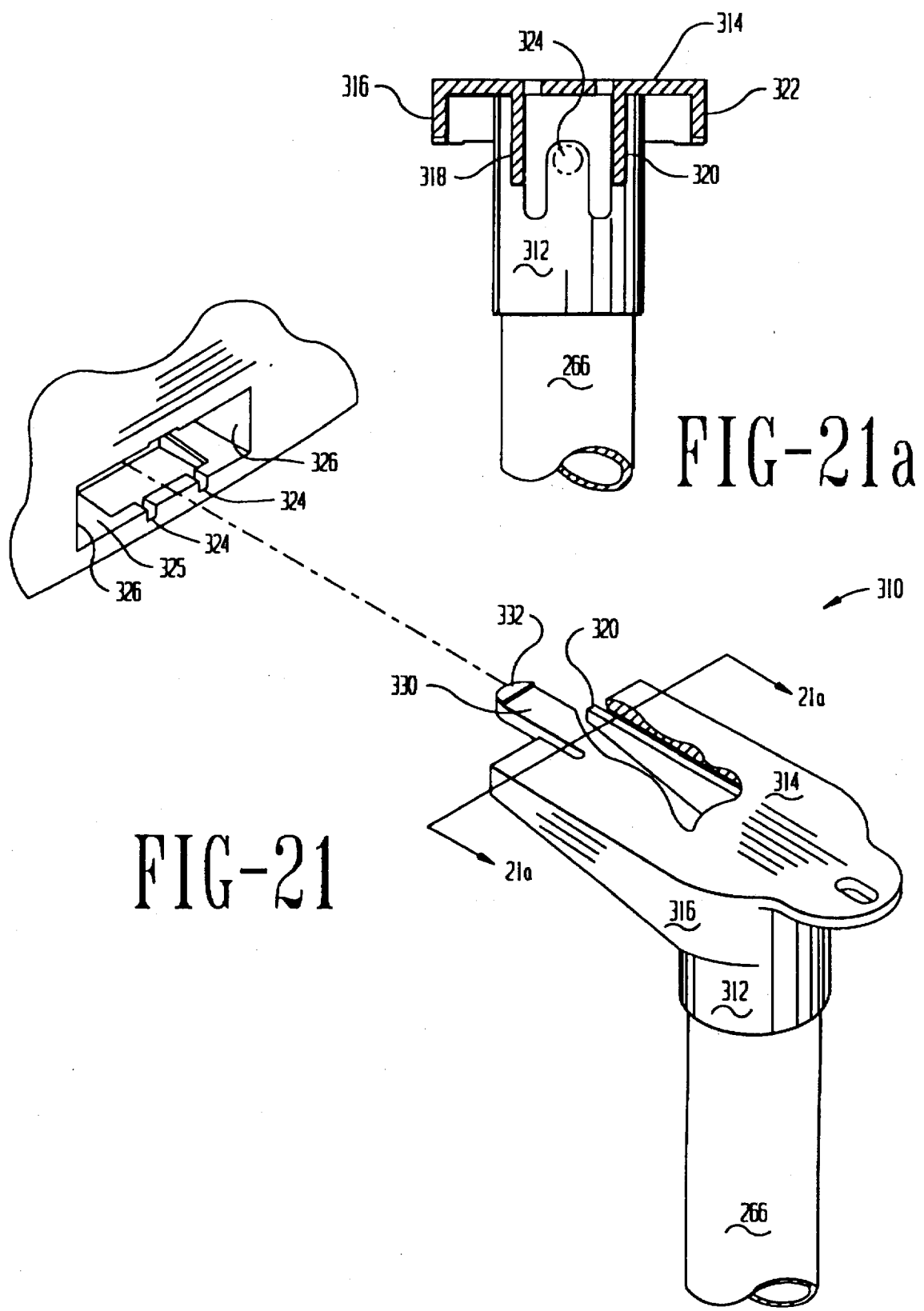

5,676,133

EXPIRATORY SCAVENGING METHOD AND APPARATUS AND OXYGEN CONTROL SYSTEM FOR POST ANESTHESIA CARE PATIENTS

CROSS-REFERENCE

This application refers to and relies upon the earlier filed provisional application entitled SOURCE CONTROL SCAVENGING SYSTEM AND APPARATUS FOR POST ANESTHESIA CARE PATIENTS, filed Jun. 14, 1995 as Ser. No. 60/000,196 and upon the earlier filed provisional application entitled OXYGEN CONTROL AND SCAVENGING METHOD, SYSTEM AND APPARATUS FOR POST ANESTHESIA CARE PATIENTS, filed Jan. 20, 1996 as Ser. No. 60/009,688.

FIELD OF THE INVENTION

This invention is directed to reduction and elimination of identified health risks to personnel and patients in health care facilities. The primary focus of this invention is the contaminants resulting from the exhalations and forced expirations of anesthetic gases and pathogens by surgical patients in the Post Anesthesia Care Unit (PACU). Another focus of this invention is the patient's ventilation, i.e., the provision for forced ventilation under emergency circumstances and the control of the oxygen-air ratio supply to the patient after surgery.

The first group of atmospheric contaminants to which this invention is directed is anesthetic gases such as nitrous oxide, halothane, enflurane, isoflurane, desflurane and sevoflurane. These anesthetics are used in the Operating Room (OR) with limited exposure to its personnel through the use of a cuffed tracheal tube which is connected to a scavenging circuit. However, upon removal of the tube, the patient continues to expel the anesthesia gases for as long as several hours. As a result, the atmosphere of the Post Anesthesia Care Unit (PACU) to which the patient is first moved after surgery, becomes contaminated with residual anesthesia gases. This contamination of the PACU atmosphere subjects the hospital staff to repeated and continual inhalation of these gases. Significantly, such gases present recognized health risks to nurses and doctors. For example, the U.S. Department of Health and Human Services issued a NIOSH ALERT in April of 1994 stating A large population of health care workers is potentially exposed to $N_2O$, and NIOSH has documented cases in which exposures substantially exceed existing RELS [Recommended Exposure Limits]. NIOSH has concluded that exposure to $N_2O$ causes decreases in mental performance, audio-visual ability and manual dexterity. Data from animal studies demonstrate that exposure to $N_2O$ may cause adverse reproductive effects. Studies of workers exposed to $N_2O$ have reported adverse health effects such as reduced fertility, spontaneous abortion, and neurological, renal and liver disease.

A second group of contaminants in health care institutions is that of pathogens, both blood borne and airborne, which are expelled by infected patients or carriers. These contaminants include droplet nuclei containing viable tubercle bacilli, the causative agent of tuberculosis.

After surgery, patients in the PACU may cough as often as once a minute. Each cough by a patient with active tuberculosis may forcefully expel, at high velocities, thousands of droplet nuclei. Such droplet nuclei contaminate the atmosphere of the PACU. Moreover, the nuclei can remain airborne and viable for hours. Significantly, this undesirable result is aggravated by removal of the tracheal tube and by suctioning required to remove oral and nasal secretions-procedures that increase the incidence of coughing and the resulting air contamination. Also aggravating the situation is the fact that the nurses, in removing the tracheal tube or suctioning the oral cavity of a patient, typically work within eighteen to twenty four inches of the patient. And though nurses may wear clear face shields to protect from splattering by a patient's cough directly into their faces, such is not believed to be adequate to protect them from either the droplet nuclei, as small as one micron, or the anesthetic gas expelled by the patients.

Further aggravating the working environment of the PACU is its size. Many Post Anesthesia Care Units are comprised of a single room with a common ventilation system accommodating twenty or more patients at a time. As a result, the pathogens expired by one patient may be communicated to other patients, some of whom have compromised immune systems.

Reduction or elimination of these described contaminants is a focal point of this invention. Significantly, the benefits of reduction of contamination with the resulting decrease in disease transmission and risk exposure to anesthesia gases are believed to far exceed the minimum cost detriment resulting from the use of the proposed invention in the Post Operative Care Unit. The disclosed invention, however, as well as its inventive components are not necessarily restricted in use to the PACU. Instead, they may have direct applicability in other heath care facilities such as operating rooms, bronchoscopy suites, emergency rooms, patient transport, physicians offices, ambulances, rest homes, etc. For example, the patient mask of this invention can facilitate safer bronchoscopic examinations by limiting contamination of the atmosphere due to patient coughs and expirations. In addition, the invention will also facilitate the application of anesthesia gases to the patient during a bronchoscopic exam and then scavenge the patient's expirations of the gas and any pathogens to the atmosphere, if desired.

A secondary focus of this invention is patient ventilation. During surgery, the surgical team and the patient had the benefit of numerous monitoring and supply devices. These include, for example, oxygen saturation monitoring with a pulse oximeter, the continuous delivery of a controlled oxygen supply, as well as a positive pressure ventilator for the patient who is not spontaneously ventilating. After surgery, the patient is normally detached from all of these devices, removed from the supervision of the surgical team and placed on a gurney for transportation to the Post Anesthesia Care Unit. Significantly, it has been established that, during this transport, many surgical patients become significantly hypoxemic (hemoglobin desaturation) because of the lack of adequate oxygen. In addition, some patients need controlled or positive pressure ventilation during this trip due to neuromuscular blocking agents, narcotic drugs, lung disease, thoracic surgery, etc. And upon arrival at the PACU, some patients need a controlled air-oxygen ratio rather than an uncontrolled ratio that is provided by nasal cannulae. As will be shown, the present inventions also focus upon and provide solutions for these problems. In addition, the ability of our invention to permit positive ventilation and effective scavenging of a patient's breathing further facilitates its use as a lower cost inhalation therapy system. Specifically, another contemplated use of our invention is the application of drugs such as nebulized pentamidine for pneumocystis carinii and ribavirin for respiratory syncytial virus pneumonia. (For the convenience of the reader, headings and subheadings are provided to provide a helpful guide to the contents of this specification. However, information on some subjects is scattered throughout the specifications, drawings and claims and could not be segregated under a specific heading).

DESCRIPTION OF THE RELATED ART

At the present time, there is little or no equipment or systems in place within the PACU to prevent the contamination of the atmosphere by either the anesthesia gases or the blood-borne and air-borne pathogens. For the most part, contamination of the air by patients lacking the diagnosis of active tuberculosis is an accepted risk. And once active tuberculosis is diagnosed, present alternatives focus upon patient isolation, ventilation, negative differential pressures, HEPA filters and germicidal UV irradiation.

These approaches are not appropriate in light of evidence that the greatest risk of tuberculosis transmission to health care workers is from patients with undiagnosed active tuberculosis. See Department of Health and Human Services, Centers for Disease Control and Prevention; "Draft Guidelines for Preventing the Transmission of Tuberculosis in Health-Care Facilities, Second Edition, Notice of Comment Period." Federal Register, Vol. 58, N1. 195, Oct. 12, 1993.

Only limited efforts have been made to control contamination due to anesthesia gases or to pathogens. Those efforts include the use of a mask connected to a vacuum manifold that, in turn, is connected to a vacuum system. The following patents are illustrative of those efforts.

U.S. Pat. No. 4,015,598 which discloses sources for nitrous oxide and oxygen, a conduit for delivering these gases to the patient through a mask that exhausts the patient's expirations to the outside atmosphere through a vacuum.

U.S. Pat. No. 4,265,239 which discloses an anesthesia machine, primarily intended for the dental office, coupled to a patient mask that, in turn is connected to a vacuum pump for disposal of expiration gases to the outside atmosphere.

U.S. Pat. No. 4,653,493 which discloses a contamination control device for connection to the expiratory side of a conventional respiratory ventilator unit.

U.S. Pat. No. 4,707,617 which is directed to a modification of a standard anesthesia mask, so as to collect and scavenge the anesthetic gases that leak beyond the face mask to contaminate the atmosphere.

While these prior efforts state or indicate the nature of the problem, none effectively meet the special needs of patients in the PACU or of the hospital staff that, day after day, is immersed in a potential environment of gases and pathogens expirated by the patients coming out of surgery.

At the present time, there are available some portable ventilator devices that can be used during the patient's transport to the PACU. Such includes, for example, the well known "Ambu" bag that can be manually manipulated to force the patient's inhalation of oxygen through a tracheal tube.

Other devices have been suggested for assisting patient ventilation after surgery. One example is U.S. Pat. No. 3,357,426 which discloses the use of a mask to deliver anesthesia as well as to assist in ventilating the patient who has been partially paralyzed by the use of anesthetics. Another suggestion is disclosed in U.S. Pat. No. 4,261,355 which comprises a T-shaped positive pressure breathing apparatus.

SUMMARY OF INVENTION

This invention provides a unique, low-cost, effective solution to contamination of the PACU and simultaneously meets the special, potential needs of the patients. It comprises a system and components that preclude the undesired contamination of the PACU at the patient source of the contaminants. The invention also eliminates reliance on the nasal cannulae to deliver a fixed oxygen enriched gas ratio to the patient. Alternatively, it can be used with an $FiO_2$ controller or blender to vary the oxygen-gas ratio as desired. Finally, the invention provides for a positive ventilation during the transport of the patient from the operating room to the PACU.

The invention includes a pliable, patient mask with a positive face seal connected through a ventilator circuit to a unique airator having a pneumatic control circuit for supplying an air-oxygen mixture and for providing a vacuum to the atmosphere outside of the hospital. In the preferred embodiment, the mask is formed of a foundation or base component for sealing engagement with the patient's face and an adapter or cover coupler. The cover coupler includes a connector for connection to conventional ventilator conduits that conduct 1) an oxygen mixture from the supply side of the novel airator to the patient and 2) the patient's expirations back to the exhaust side of the airator and then to a vacuum source within the PACU.

To meet the special needs of the surgical patients, the base and adapter components are sealingly assembled to one another in a way to facilitate immediate removal of the adapter portion in an emergency such as an accumulation of fluids that has interrupted the patient's breathing. Alternatively, the mask base is provided with loose, accessible pull tabs that may be grasped to strip the entire mask unit from the patient's face. In addition, the cover adapter of the mask may be provided with a thin sealing membrane through which a suction catheter may be sealingly inserted into the patient's mouth or nasal passages to remove secretions and undesirable fluid buildup while maintaining the integrity of source control of anesthetic gases and pathogens.

This mask is connected to the airator device of our invention. This airator includes a unique, low cost monitor-manifold for receiving and valving an air/oxygen mixture to the patient and for scavenging the patient's exhalations directly to the outside atmosphere. The airator includes safety precautions against excess positive and negative pressures and permits the delivery of a controlled oxygen-gas mixture to the patient. Preferably the monitor is also provided with diagnostic equipment such as reservoir-ventilator bags to permit a visual indication of the patient's breathing and the system's proper operation.

The present invention also facilitates positive ventilation of the patient during the trip from the operating room to the PACU and simultaneously reduces the possibility that patients will become hypoxemic during transport to the PACU. Positive ventilation of the patient is simplisticly effected by a manually operated tube ventilator or "oxyvent" that is specially designed to connect a portable oxygen tank to either a tracheal tube or the mask of this invention. The oxygen deficiency and resulting hypoxemia is also overcome by the use of the mask of this invention with a portable oxygen tank. To prevent pathogen contamination of the hospital facilities during the patent's transport to the PACU, a bacteria filter is used in conjunction with the tube ventilator.

The apparatus of this invention further achieves a novel method of providing inhalation therapy of nebulized drugs to patients with respiratory problems. For example, the invention can be used as a very low cost, safe and effective method of administering drugs such as pentamidine to patients having pneumocystis carinii and ribavirin to patients having respiratory syncytial virus pneumonia.

Finally, the inventions of this disclosure have direct application in bronchoscopy suites in that the apparatus permits the application of anesthesia gases to patients through the airator and mask while simultaneously scavenging his expirations and permitting the bronchoscopic examination instruments to be inserted into the patient's lungs through the sealing membrane of the mask.

Accordingly, the present invention is intended to achieve the following objects and to serve the following purposes:

1. An effective method and system for precluding contamination of the PACU by scavenging patient exhalations of anesthetic gases and pathogens directly to the atmosphere outside the hospital;
2. A source control system for minimizing exposure of the hospital staff and other patients in the PACU to expelled anesthetic gases and pathogens;
3. A pliable mask that provides a positive, adhesive seal to the patient's face and does not impede or adversely affect the possible needs of the patient such as catheter suctioning of undesirable fluid buildup;
4. A pliable mask that does not annoy or discomfort the patient and has provisions for fast, emergency removal and access to the patient's mouth and nasal cavities;
5. A patient mask component that simultaneously facilitates coupling of a ventilator circuit to a patient and as well as insertion of a suction catheter through a sealable aperture to remove undesirable fluids from the patient's nasal passages and mouth;
6. A patient mask having an adhesive formed of a thick foam that can be used in lieu of the present anesthesia mask to provide the multiple functions of a low cost, cushioned anesthesia mask in the OR and an scavenging mask in the PACU;
7. A patient mask having a removable air tube cushion that can be used in lieu of the present anesthesia mask to provide the multiple functions of a low cost anesthesia mask in the OR and a scavenging mask in the PACU;
8. A unique diagnostic airator and manifold for delivering air-oxygen to a patient and for vacuuming exhalations directly to the atmosphere, the airator incorporating several safety devices and having the capability to accept a plurality of respiratory visual indicators;
9. A low cost system and components that are cost effective in substantially reducing anesthesia gas contamination in the PACU and in maintaining such units in full compliance with all OSHA and NIOSH standards;
10. A system with components that are cost effective in precluding pathogen contamination in the PACU and other areas of a health care facility;
11. A simple, low cost apparatus and novel method of providing inhalation therapy to a patient;
12. A novel anesthesia gas and scavenging system which simultaneously permits bronchoscopic examinations by insertion of examination devices through the thin sealing membrane of the mask and into the patient's lungs; and
13. A low cost, manually operated tubular ventilator or "oxyvent" for providing supplemental oxygen and, if needed, positive pressure ventilation to the patient and for forcing patient inspiration when necessary, particularly during the patient's trip from the OR to the PACU.

DESCRIPTION OF THE DRAWINGS

The manner in which these objectives and desirable purposes can be obtained from the instant invention is explained in the following specification and the attached drawings in which:

FIG. 3 is an exploded, perspective view depicting most of the components of the embodiment of FIG. 2;

FIG. 4 is an exploded, perspective view depicting the components of a second embodiment of the face mask of this invention;

FIG. 5 is an exploded, perspective view depicting the components of another embodiment of the face mask of this invention;

FIG. 10(a) is an enlarged cross sectional view of the outer edge of the mask base of FIG. 10;

FIG. 17 is an exploded view, in perspective, of the front of one embodiment of the airator housing and front plate of this invention, the front plate being depicted in a perspective view and the housing in a side elevational view;

FIG. 18 is an exploded view, in perspective, of a one-way valve used in the airator invention of this disclosure;

FIG. 19 is an enlarged view, in perspective, of the control knob and valve for the vacuum connection of the airator manifold;

FIG. 20 is a sectional view taken along the lines 20—20 of FIG. 17 to further illustrate a portion of the vacuum circuit;

FIG. 21 is an exploded view, in perspective, of the latching mechanism of the pedestal lock or mounting assembly for the airator of this invention;

FIG. 21a is a plan view, in section, taken along the lines 21a—21a of FIG. 21;

DETAILED DESCRIPTION

Figure 1:
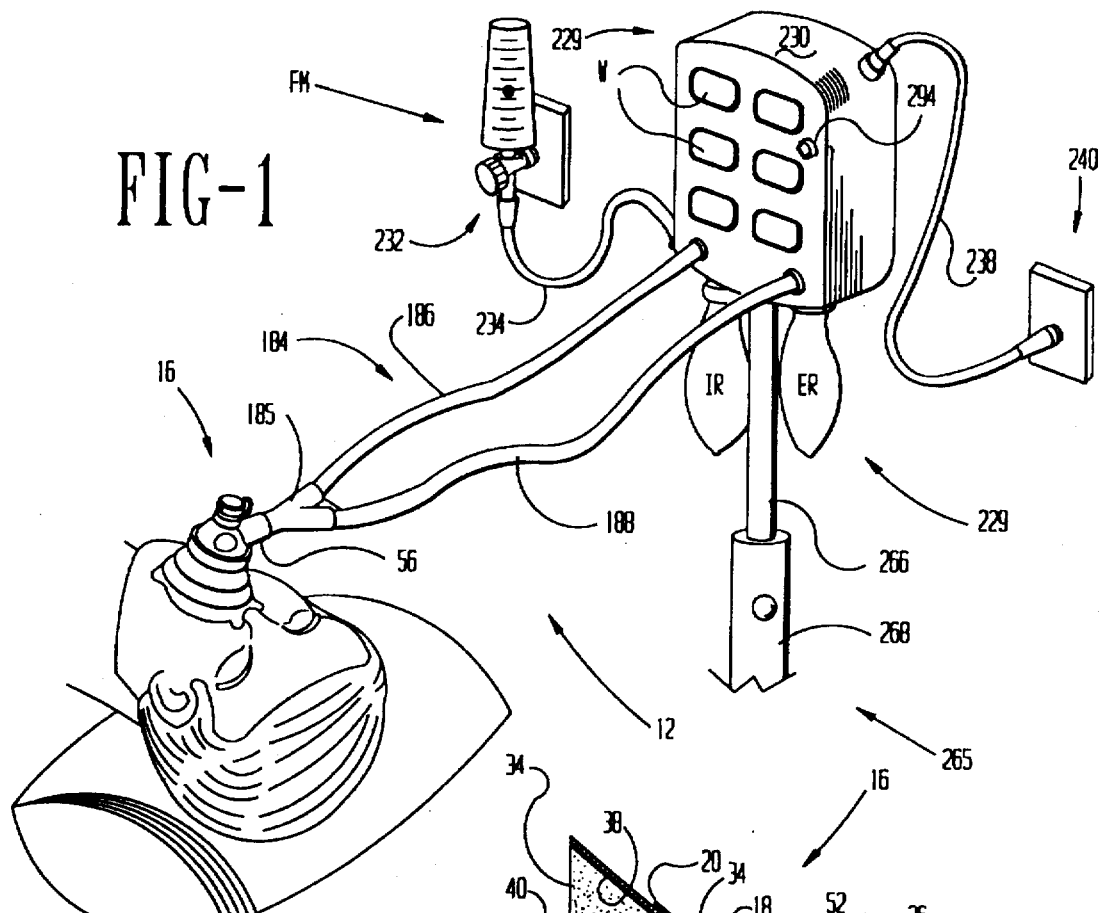
FIG. 1 is perspective view of a portion of a typical Post Anesthesia Care Unit (PACU) depicting a patient connected to the scavenging system of this invention which includes a patient mask, a ventilator circuit and an airator for delivering oxygen to the patient while scavenging patient exhalations and anesthesia gases through a vacuum connection to the external atmosphere.

An overview of the scavenging-diagnostic system of this invention is illustrated in FIG. 1 which depicts a patient in a Post Anesthesia Care Unit (PACU). As shown, the patient is connected to the scavenging and diagnostic system 12 of this invention. This system includes a mask 16 sealingly engaged to the patient's face, a ventilator or airway conduit or circuit 184 connecting the mask 16 to an airator 229. This airator comprises a manifold circuit within a housing or shell 230 which is further connected to oxygen and vacuum ports, 232 and 240 respectively. Generally, this system receives oxygen from the oxygen port 232 through flow meter FM mounted on the wall of the PACU, and delivers it through the conduit 234, the airator 229, the ventilator conduit 184 and mask 16 to the patient. Upon the patient's exhalation, the expired gas travels through the mask 16 and airway circuit 184 back to the airator 229 which discharges it to the vacuum conduit 238 and vacuum source 240 that is connected to the outside atmosphere.

An important factor in precluding contamination of the PACU atmosphere is the sealing effectiveness of the scavenging system 12. That sealing effectiveness is primarily dependent upon the design of the mask 16 whose configuration must take into consideration a combination of features, including, among other things: visibility of the patient's mouth and nasal area, immediate access to the patient's mouth without necessarily losing the sealing contact between the mask and the patient's face, a small aperture (or thin flexible diaphragm that can be pierced) to permit insertion of a suction catheter into the patient's mouth and nasal passages to remove fluid buildup, the ability of the mask and seal to withstand the force applied by a patient's coughing, non-irritation of the patient or his facial skin, etc.

The Mask Embodiments

Figure 2:
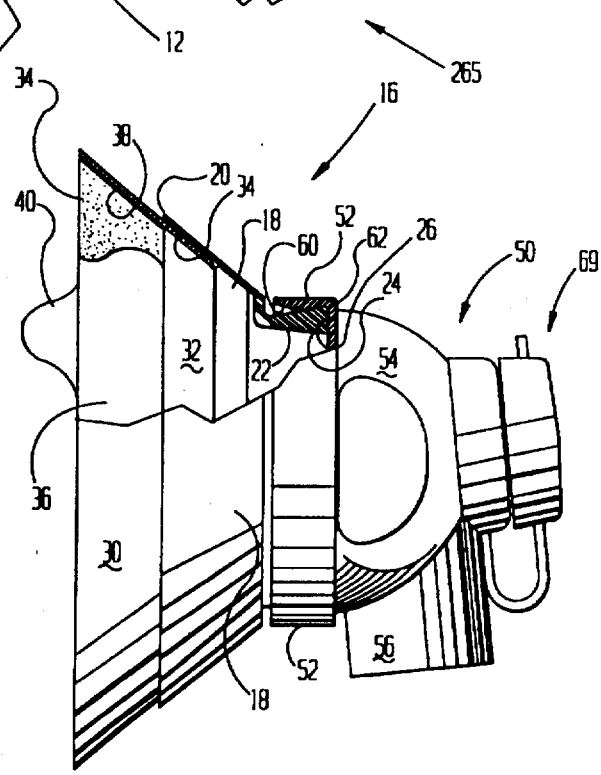
FIG. 2 is a side elevational view, with portions broken away, of one embodiment of the face mask of this invention.
Figure 6:
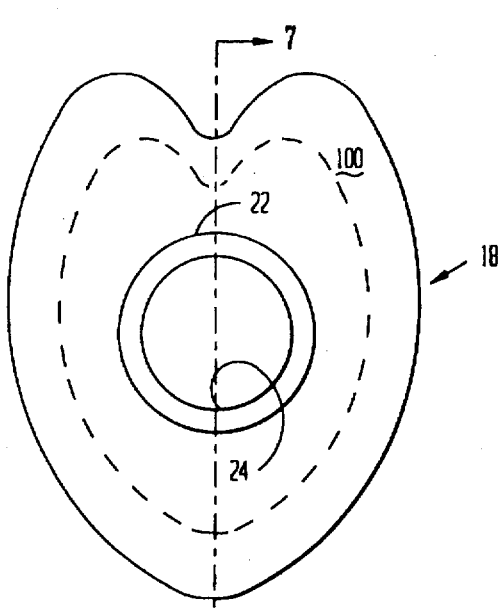
FIG. 6 is a plan view of a mask base or foundation of another embodiment of this invention.
Figure 7:
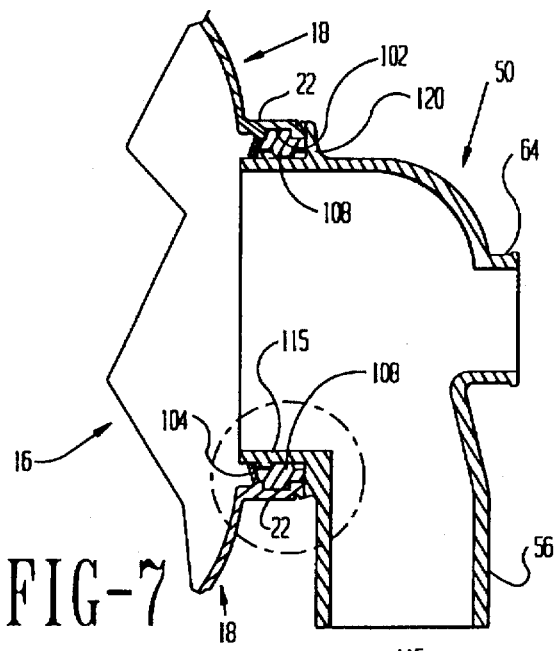
FIG. 7 is a side elevational view taken through a vertical center line of the mask of FIG. 6 and of an associated adapter.

The foregoing features can be achieved with the various mask embodiments of this invention. One of those embodiments is depicted in FIGS. 2 and 3. This mask includes a mask base or foundation 18 which is molded into a generally frustoconical shape to define a cavity that will receive and cover a patient's nose and mouth. The base member 18 extends from a large diameter edge 20 to the cavity and communicates through a connector 56 of adapter 50 to the ventilation circuit 184. Preferably, the base extends to a neck or flange 22 of a lessor diameter which defines a generally circular opening that has a thicker, more rigid wall section as shown at 24. Contrary to the rigidity of the flange 22, the edge 20 is thin, pliable and has little memory so as to readily conform to the face of the patient in sealing engagement without stress or discomfort. Its thickness may be 25 mils or less.

Preferably, the base 18 is molded of a generally clear, transparent plastic or rubber such as a commercially available transparent polyvinyl chloride, a polyethylene, a polypropylene including a random co-polymer polypropylene, a polyurethane or a thermoplastic rubber. Illustrative plastics that are believed to be acceptable include Compound 0-4129, a polyvinyl chloride sold by Ellay, Inc. of the City of Commerce, Calif., a polypropylene random copolymer such as that sold under the trade mark Affinity® by Dow Chemical Co. of Midland Michigan, a polyolefin elastomer, also sold by Dow Chemical Co. under the trademark Engage® a plastomer sold under the trademark Exact® by Exxon Chemical of Houston, Tex., Kraton®, a styrene-butadiene-stryene (SBS) manufactured and sold by Shell Oil Company, and C-Flex®, an elastomer sold by Consolidated Polymer Technologies, Inc. of Clearwater, Fla. As noted earlier, the preferred material for the mask base is a thermoplastic rubber. One such acceptable rubber is sold by GLS Corp., 740B Industrial Drive, Cary, Ill. 60013 under the designation Dynaflex™ 2701.

While these and other plastic compositions may be used to provide the desired clarity, transparency and pliability, each should also accept and sealingly bond with an adhesive. In the embodiment of FIGS. 2–5, a frustoconical shaped film section 30 is bonded to the base 18. The external side of the film 30 has an annular area 32 which carries an adhesive 34 for bonding to the peripheral edge 20 of the mask base 18 to join the two together. To then seal the mask to the patient's face, an internal annular area 36 carries an adhesive 34 that, until use, is covered by backing 38. To apply the mask to the patient, the backing 38 is stripped away from the film 30 and the mask 16 is generally centered upon the patient's face. Light pressure is then applied to section 36 of the film 30 to obtain a sealing engagement between the patient's face and the mask 16 so as to preclude the escape of patient exhalations from between the face and the film 30.

Since one of the primary uses of this mask is for patients coming out from under anesthetic gases, our invention includes at least one quick detach device that will permit immediate access to the patient's face in the event of emesis, airway obstruction or acute respiratory insufficiency. With the embodiments of the base units 18 depicted in FIGS. 3–5, the quick detach device includes one or more tabs 40 that extend from outermost periphery of the film 30. To insure that these extensions 40 are easily grasped, they are free of adhesive to avoid adhering to the face of the patient. Preferably, the two pull tabs 40 are affixed adjacent the outer lateral perimeter of the mask. Those skilled in the art will appreciate that other quick detachable devices may serve as acceptable substitutes. For example, a generally vertical score line could be formed or die stamped into the mask base 18 to facilitate tearing the mask open.

This film section 30 and its adhesive should be hypoallergenic. For example, the film may be a polyethylene film that carries a conventional hypoallergenic, non-sensitizing acrylate adhesive. The adhesive may be applied as a spray or by rollers, etc. and the film can be cut, die cut, thermoformed or stamped into the desired shape. Conventional transfer systems may be used to apply the film 30 to the mask base 18.

As the mask extends from the film section 30 towards the circular opening 24, its cross sectional thickness may increase to provide rigidity and to facilitate handling. This increased wall thickness of the mask base 18 serves the dual purposes of providing rigidity against collapse upon a patient's inhalation and of providing rigidity to facilitate a sealed interlock or coupling of the opening 24 to an associated cover adapter 50.

The cover adapter or coupler 50 serves primarily as a coupler between the mask base 18 and the ventilator circuit 184. It includes a collar 52 that is joined to a generally spherical section 54 to which is integrally molded a conduit connector 56 for connection to the ventilator circuit 184. The connector 56 is sized to sealingly engage standard ventilator or airway tubing such as that illustrated at numeral 184 of FIG. 1. To facilitate cost savings, this ventilation circuit would, preferably, be the same ventilation circuit that was used by the anesthetist during surgery. Such ventilator circuits have an ASTM 22 mm external diameter standard-tapered male fitting that mates with an ASTM 22 mm standard tapered female ID of connector 56.

The adapter or coupler unit 50 is designed to meet several anticipated needs of some patients. Significantly, it is also an alternative backup "quick detach" device. The adapter 50 can be quickly and easily removed to permit the patient's mouth to be suctioned or drained through the aperture 24. Alternatively, the adapter 50 may also be provided with cover cap 69 that will also permit limited access to the patient's mouth as further described in conjunction with FIG. 4.

The exploded views of FIGS. 3–5 illustrate three different sealing engagements between the adapter 50 and the flange 22 of the base 18. The embodiment of FIGS. 2 and 3 illustrates the simplest sealing arrangement. It is analogous to a lip type seal in which the diameter of the flange or neck 22 increases as it extends away from the base 18 to terminate in the opening 24. The flange or neck 22 and the opening 24 are intended to telescope into a collar 52 of the adapter or coupler 50. As best viewed in the prior FIG. 2, the collar 52 has an internal surface that begins with an oversize diameter or flare 60, extends to a reduced diameter as shown, and terminates in a larger diameter 62 which serves as a seal seat.

In mounting this adapter 50 onto the mask base 18, the adapter is first positioned over the flange 22 of base 18. Then pressure is applied to the adapter 50 to cause the collar 52 to telescope over the outer edge 26 of the opening 24 and into sealing engagement. As the collar 52 telescopes over the flange 22, the outside edge 26 of flange 22 is first caused to flex inward by the reduced diameter of the collar 52 and, as telescopic movement continues, the outside edge 26 of the flange 22 flexes outward into sealing engagement with the larger diameter of the collar 52 which serves as a seal seat at 62. The flexing of the circumferential lip 26 during assembly serves two purposes. First, it provides a "feel" or "sensing" to the assembler or nurse that the seal has, in fact, been affirmatively seated. Second, the thickness of the flange or neck 22 is sufficiently large to provide a flexural stress forcing the lip 26 into tight sealing engagement with the seat 62 of the collar.

The cover adapter 50 has a short cylindrical extension 64 (see FIG. 3) which also provides access to the patient's mouth through an aperture 68. This extension 64 terminates in a flange 66 that sealingly receives the access cap 69 and closes the aperture access 68 of the extension. The access cap 69 may be a one piece molded unit comprised of an annular fitting 70 having an internal annular grove (not shown) that receives the flange 66 of the extension 64. The access cap 69 also includes a hinge strap 72 and a cap 74. The annular fitting 70 is also provided with an external fitting flange 76 that mates with an annular grove 78 in the cap 74 in a snap type sealing relationship. This access cap 69 provides quick access to the patient's mount for a suction catheter. As discussed in connection with FIG. 4, this access cap may be further provided with a pliable cover film 80 to limit contamination of the atmosphere.

The face mask embodiments of FIGS. 4 and 5 are substantially the same as that of FIG. 3 except for the sealing connection between the adapter 50 and the mask foundation 18. In FIG. 4, an O-ring is used to provide the sealing connection. To use the O-ring seal, an annular groove 86 is machined or molded into outside cylindrical surface of the neck or flange 22 of the base 18. A corresponding annular grove 88 is machined or molded into internal cylindrical surface of the collar 52. And, after molding, an O-ring 90 is inserted into one of the grooves 86 or 88. Thereafter, the quick detach adapter 50 may be telescoped over the flange 22 of the base until the O-ring 90 has seated in both grooves to define an effective seal.

Those skilled in the art will appreciate that the O-ring 90 and the depth of the groves 86 and 88, together with the hardness of the plastic material, can be selected to insure a detent type lock that will hold these component in sealing engagement regardless of the force of a patient's cough or sneeze. Preferably, all embodiments will be provided with a detent or interlock that is mechanical in nature and comprises more than a mere "friction fit" or "press fit." Alternatively, those skilled in the art will also appreciate, in combination with the O-ring, a bayonet detent or threaded connection between the adapter 50 and the base 18 may be used to lock these parts together. The O-ring may be formed of Viton® or a silicone elastomer and is sized such that upon assembly of the adapter 50 with the mask base 18, it is placed under sufficient compressive force by the limited depth of the O-ring groves as to reduce its cross sectional dimension by 1.5 to 12 per cent and to effect a gas tight seal. (Viton® is an elastomer manufactured and sold by E. I. dupont de Nemours of Wilmington, Del.)

The embodiment of FIG. 4 also discloses the addition of a thin pliable sheet film 80 extending across the opening 68 of the extension 64. Preferably, this membrane 80 includes a very small molded aperture 82 through which a nurse or physician may sealingly insert a suction catheter into the patient's mouth without removing the adapter or interrupting oxygen flow to the patient or permitting contaminated exhalations to escape to the atmosphere. Alternatively, aperture 82 may be omitted by forming the membrane 80 of an elastomer that is resistant to tear propagation so as to permit the nurse or physician to pierce the film, and insert the catheter while maintaining a sufficient seal. As long as an effective seal is provided, those skilled in the art may substitute other types of seal components and surfaces in lieu of the membrane as well as the flange and groove arrangement that is disclosed. However, it should be noted that molding of the illustrated components may require a compound that has more elastomeric than plastic characteristics in order to strip some of the parts from the mold.

The embodiment of FIG. 5 discloses yet another seal arrangement between the base 18 of the mask 16 and the adapter 50. This seal arrangement includes camming lugs 92 positioned on the outside cylindrical surface of the base flange that can be inserted into the internal circumference of adapter collar 52. After insertion, the adapter is then rotated and camming surfaces 96 within the adapter cooperate with the camming lugs 92 to not only lock the two parts together but to pull the top surface 27 of flange 22 into tight sealing engagement with a mating sealing surface of the adapter 50 (not shown).

Without further disclosure, those skilled in the art of plastic molding will well appreciate further modifications and alternatives of the illustrated seal arrangements depicted in FIGS. 2–5. For example, the masks 16 of the embodiments of FIGS. 3–5 also disclose a recess 42 in the tape 30 for fitting over the patient's nose. Such may facilitate sealing of the mask to the patient's face.

FIGS. 6–9 depict an alternative mask design for the system of the present invention. This embodiment serves the same purposes and functions but may well provide some manufacturing advantages. In large part, the objective is to use a thinner plastic or elastomer that will better conform to the patient's face and yet provide excellent coupling of the base to the adapter. Another objective is to use less material. Consequently, this embodiment comprises a very thin, pliable base unit to which is affixed a seal-lock insert to provide the desired rigidity for handling and for sealing.

In the depicted embodiment of this alternative, the mask base is generally formed of a very thin material that will conform to the patient's face and eliminate the need for a separate adhesive film. Consequently, the adhesive may be applied directly to a peripheral area of the base indicated at 100. Like the prior embodiments, the foundation or base 18 extends upwardly to define neck or flange 22 that terminates in a generally circular opening 24.

The flange or neck 22 of base 18 of this embodiment is provided with an internal groove 102 for receiving a rigid annular insert 108. In addition, a lip type seal flange 104 is integrally molded around the internal circumference of the neck 22. This seal flange 104 extends radially inward to sealingly engage the external circumference of the assembled quick detachable adapter 50 and to preclude the escape of anesthetic gases or pathogens from the system.

The insert 108 may be molded of a polypropylene or, preferably, a conventional polycarbonate material such as Lexan® 123R from the General Electric Co. Such not only provides rigidity to the very pliable elastomer-plastic, it also serves as the locking connector between the base 18 of the mask 16 and the adapter 50. To serve the rigidity functions, the insert 108 is provided with an external annular rib 110 that is inserted and seated into the annular groove 102 of the neck 22 of the mask base 18. Although an adhesive might be used to maintain the insert 108 in the groove 102, an interference fit is preferred. Alternatively, the insert may be inserted into the mold for the base 18 of the mask 16 with the mask base 18 being molded around the insert.

To serve its locking function, the insert 108 is provided with an interrupted internal locking rib 112 that forms a part of a bayonet detent mechanism. This locking rib 112 is interrupted by vertical slots 114 which receive and permit locking projections 116 of an internal collar 115 of the quick detachable coupler 50 to pass therethrough. Upon rotation of the adapter 50, the top surface 116a lower surface 112a of the engage the lower surface 112a of the internal rib 112 of the insert. The interlocking relationship between these two surfaces locks the detachable adapter 50 to the mask base 18.

A combination spring-face seal is used to hold the surfaces of the locking rib 112 in contact with the surfaces of the projections 116. This spring-face seal takes the form of a raised face or surface projection 118 of opening 24 of the flange of the mask base 18. (See FIG. 9). The spring action of this projection 118 is provided by the elastomer properties of the molding compound. Upon insertion and rotation of the adapter collar 115 into the insert 108, surface projection 118 engages a surface 120a of the radial flange of the mask adapter 50 to resiliently apply an axial force to surface 118. The compressed material under the surface 118 then acts as a spring attempting to expand so as to hold surface locking surfaces 116a and 112a in locking contact with one another. In addition, the engagement between surfaces 118 and 120a results in a face seal that further precludes and insures against leakage of gas or bacteria from between the adapter 50 and the base 18 of the mask.

Figure 8:
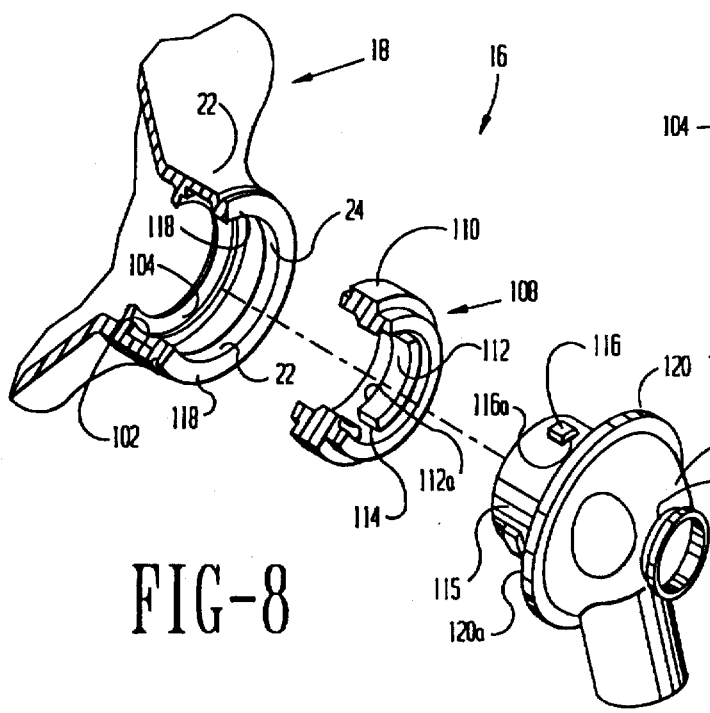
FIG. 8 is an exploded perspective view with portions broken away of the embodiment of FIGS. 6 and 7.
Figure 9:
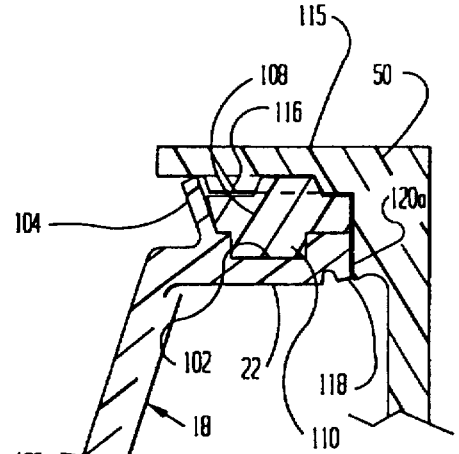
FIG. 9 is an enlarged view of the circled portion of FIG. 7.

As reflected in FIGS. 8 and 9, one benefit of this design is the provision of the two separate seals between the adapter 50 and the base 18. As noted above, one seal is the radial type lip seal 104 which is the preferred seal. The second seal, if desired, is the face seal resulting from the engagement of surfaces 118 and 120.

Those skilled in the art will appreciated that the various parts of the interconnection of the embodiment of FIGS. 6–9 can be reversed or interchanged. For example, in this embodiment, the collar 115 of the adapter is internal relative to the flange 22 of the mask base 18. However, in the earlier embodiments, the collar 52 of the quick detachable adapter was an external collar that telescoped over the flange 22 of the mask base.

Figure 10:
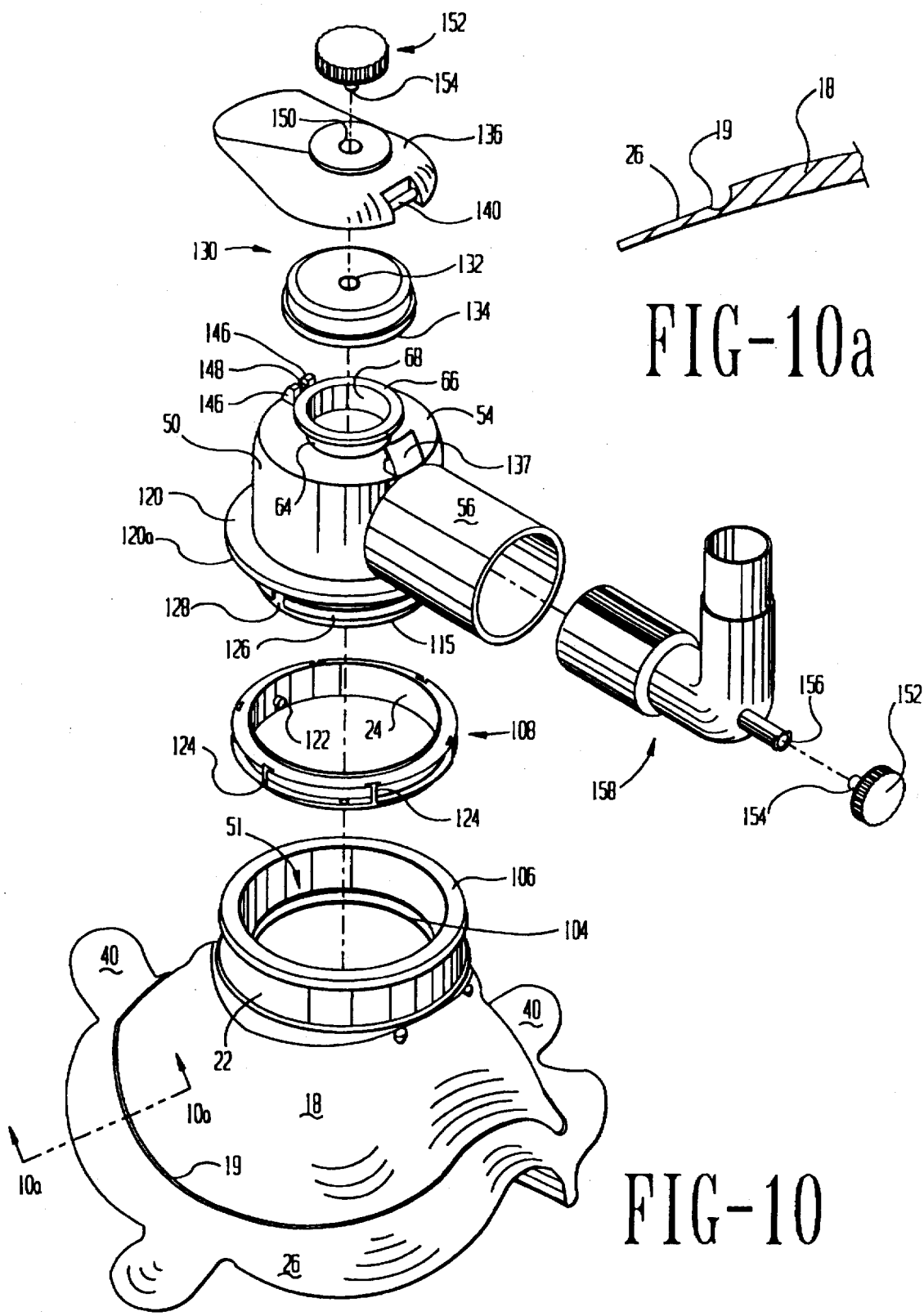
FIG. 10 an exploded view in perspective of a preferred embodiment of the face mask invention with a standard elbow coupler inserted into the mask connector and ready to be reconnected to the ventilator circuit.

The preferred mask embodiment of this invention is depicted in FIG. 10. This embodiment includes the base or foundation 18 with an integrally formed outer edge 26 which carries one or more tabs 40 for a quick removal of the mask from the patient. To better facilitate the sealing of the outer edge 26 to the patient's face, the underside or patient side of the edge is provided with a hot melt pressure sensitive adhesive, an acrylic polymer sold as composition HRJ-10127 by Schenectady International Inc. of Schenectady, N.Y. 12301. We have found that this adhesive composition is compatible with the preferred mask base composition over a substantial shelf life. That preferred plastic composition is a thermoplastic rubber sold by GLS Corp., 740B Industrial Drive, Cary, Ill. 60013 as Dynaflex® 2701. This adhesive may be applied manually to the outer edge 26 or automatically by a robot. The bond may be improved by providing a rough texture to the surface of the mask or by subjecting the mask to the well known and conventional "corona" treatment.

Separating the outer edge 26 from the base or foundation 18 is recess or hinge 19. We have found that this hinge or recess 19, which has a reduced thickness of approximately 10 mils, enhances the flexibility and conformity of a thicker edge 26 to the patient's face. Significantly, this hinge achieves this conformity while simultaneously eliminating molding problems that have resulted from molding the edge with a lesser cross-sectional thickness. Indeed, substantial problems have resulted in trying to force the molten plastic to flow and uniformly fill a cavity defining the outer edge with a cross sectional thickness of less than 10 mils.

Accordingly, this thin recess-hinge permits the desired flexible conformity to the face while simultaneously permitting the outer edge to have a greater thickness.

The base extends upward for sealingly receiving a quick detachable, cover coupler 50 to define a central cavity 51 extending over the patient's nose and mouth. This base 18 is molded about a hard insert 108 that is formed of a polycarbonate material. The hard insert 108 is also injection molded and is provided with two diametrically opposed lock pins 122 on its internal circumference and a plurality of vertical recesses 124 having a narrow opening that widen as the recesses extend into the insert 108. After being formed, this insert 108 is mounted on a male projection of a mold and extended into a female section to define the mask base cavity. The thermoplastic rubber is then injected into this cavity to form the mask base 18. Injection of the molten thermoplastic under high pressure causes the resulting mask base 18 to have an integral-like mechanical interlock with the insert 108.

As shown in FIG. 10, the resulting mask base 18 has two seal surfaces for sealing engagement with the cover adapter 50. These are a primary lip type radial seal 104 that extends circumferentially around the internal diameter of mask base just below the insert 108 and a secondary end face seal 106.

Like the embodiment of FIG. 9, the cover adapter 50 of the embodiment of FIG. 10 is formed of a hard, clear polycarbonate. It has a generally spherical section 54 that carries a lower annular flange 120 having a bottom sealing surface 120a for mating with the secondary seal surface 106 of the base unit 18. A collar 115 extends from the annular flange 120 downward to be sealingly engaged by the annular lip seal 104 of the mask base 18. Between the collar extension 115 and the flange 120 is an annular locking rib 126 which has two interruptions 128 for receiving the lock pins 122 of the locking insert 108. Insertion of the collar 115 of the cover 50 into the insert 108 and subsequent rotation sealingly locks the adapter 50 to the base 18. The lock is effected by the engagement of the lock pins 122 on the top of the locking rib 126 of the adapter and the seal are effected by the engagement of lip seal 104 with the bottom of the collar 115. In addition, a second seal can be effected by the engagement of the radial seal surface 106 with the flange 120a of the cover.

As with the prior embodiments, an annular extension 64 extends upwardly from the coupler 50 and terminates in an annular flange 66. A separately molded annular sheet or rubberlike cover 130 extends across the opening 68 of the extension 64. Preferably, this cover 130 is also molded of thermoplastic rubber, Dynaflex 2701. In addition, it is formed with a internal annular flange (not shown) that seats under the flange 66 to lock the cover 130 to the extension 64. As with the earlier embodiments, this thin cover 130 has a central aperture 132.

Figure 11:
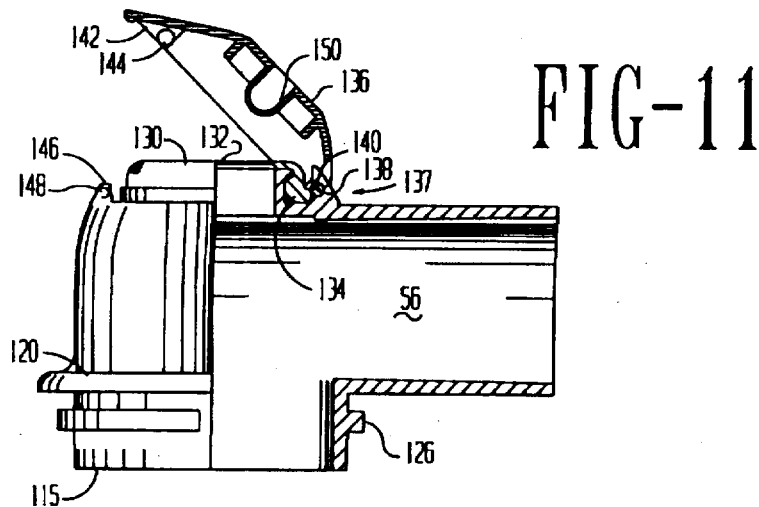
FIG. 11 is a side elevational view, with portions shown in section, of the cover adapter of FIG. 10.

A rigid access cap 136 is hingedly mounted on the coupler 50 by a hinge 137 which is best depicted in FIG. 11. This hinge 137 has a semi-cylindrical opening 138 for receiving an elongated pin 140 which is integrally molded into the access cap 136. The cap 136 and pin 140 are locked into the opening by a circumferential flange 134 of the cover 130 which extends over the extension 64.

To maintain the access cap 136 in the closed position, a detent mechanism is utilized. This mechanism may include a web 142 molded into the cap (see FIG. 11) having detent recesses 144. Upon pivoting the access cap 136 to the closed position, the web is forced between two ears 146 which have small protrusions 148 to engage the recesses 144 and lock the access cover 136 in the closed position.

The top surface of the access cap 136 is also provided with a deep recess 150 for receiving a plug 152 with a plug extension 154. This plug is supplied for the convenience of the physician who may need it to plug sampling apertures that were used during surgery to monitor the patient's carbon dioxide ($CO_2$). As shown in FIG. 10, for example, an elbow 158 that has an aperture 156 for delivering samples of the patient's exhalation's to a carbon dioxide ($CO_2$) monitor may be attached to the mask. This elbow was originally provided with a plug in its new condition, but the plug is often discarded. By providing a new plug 152 with the mask, this invention eliminates the inconvenience of searching for the discarded plug for reinsertion to preclude exhalation of anesthesia gases to the atmosphere.

Figure 12:
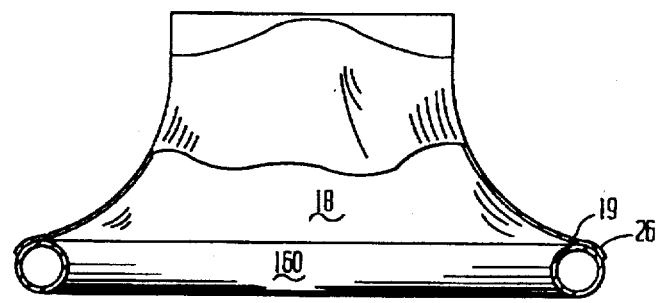
FIG. 12 is a modified side elevational view of mask base with portions broken away, the modifications including a tubular air cushion removably bonded to the edge of the mask so as to permit its use as an anesthesia mask in the OR and then to permit removal of the air cushion for subsequently bonding of the mask to the patient's face for use in the PACU.

FIG. 12 depicts a modified base 18 of the mask assembly of this invention. This modified base comprises a tubular air cushion 19 affixed to the hot melt adhesive (not shown) that is placed on the patient side of the outer edge or lip 26. Such air cushions comprise a part of the conventional anesthesia face masks that are widely used during surgery by placing and holding them, under limited manual pressure, over the mouth and nose of the patient during surgery. By temporarily bonding a separate tubular air cushion 19 to the mask of this invention, the anesthetist is provided with a substitute anesthesia face mask that may be used with the ventilator conduits 184 to connect the patient to the anesthesia machine. To accomplish this result, the separate air cushion 160 is, initially, adhesively bonded to the hot melt adhesive of the edge 26 to facilitate the use of this mask during surgery. After surgery, the air cushion 160 is merely stripped away from mask base 18 and the mask edge 26 with its hot melt adhesive is then sealingly affixed directly to the patient's face. As will be appreciated, the use of such an air cushion 160 in conjunction with this invention will clearly eliminate the need and cost for the separate conventional anesthesia mask with its integral air cushion and will simultaneously facilitate connection of the patient to the oxygen ventilation-scavenging system of this invention.

Figure 12A:
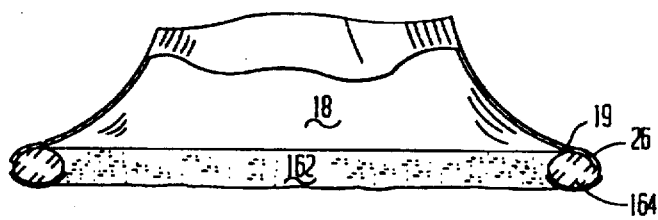
FIG. 12a is a modified side elevational view of the mask base in which the adhesive takes the form of a thickened foam bead.

FIG. 12a is another modified embodiment of the mask foundation 18. This embodiment includes a foamed adhesive bead 162 to provide a cushion for the mask. Such a bead is formed of the acrylic polymer adhesive HRJ-10127 of Schenectady International by mixing it with nitrogen for, preferably, an approximate 70% reduction in weight per unit volume. Such mixing can be effected in devices provided by the Nordson Company of Duluth, Ga. Afer mixing, the foam adhesive is extruded in the bead 162 around the inner surface of the edge 26. If desired, a release liner 164 or backing strip may be applied to the foam bead 162 as shown in FIG. 12a.

Figure 12B:
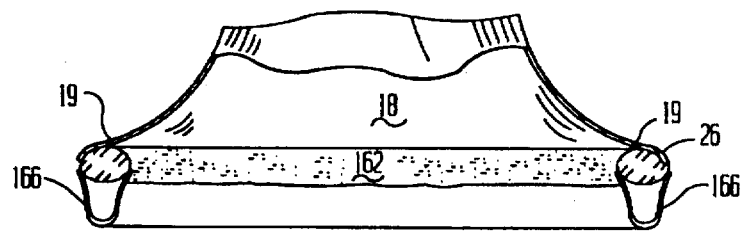
FIG. 12b is a modified side elevational view of the mask base in which an air cushion is added to the thickened foam bead to enhance use of the mask as an anesthesia mask in the OR with subsequent removal of the air cushion to permit the mask to be sealingly bonded to the patient's face for use in the PACU.

A further embodiment of the mask base is depicted in FIG. 12b. In this embodiment, a generally U-shaped elastic cushion strip 166 is molded and then affixed at its upper extremities to the foam bead 162. The cushion strip then serves two purposes. First, it enables the mask to be used in the OR as an anesthesia mask in which the cushion is manually pressed against the patient's face to define a pressure seal for the administration of anesthesia gases as needed. Second, the cushion strip 166 can be stripped from the foam adhesive 162 after surgery so that the mask, through the exposed adhesive bead 162 can be adhesively sealed to the patients face to facility the scavenging function of the mask and system.

Although it is not a preferred mask component of this scavenging system invention, those skilled in the art will also appreciate that a conventional anesthesia face mask can be effectively incorporated into and used as a component of this apparatus and system invention. Such conventional anesthesia face masks are well known to the industry. Illustrative are the masks identified by a base catalog number 43410 and sold under the trademark Ultra-Fit™ by BriGam Medical Inc., PO Box 1009, Morganton, N.C. 28680-1009. Such masks have a base defined by a tubular air cushion that fits around the mouth and nose of the patient. From this base, the mask extends upward to define a cavity terminating in a conduit connector. While such masks have no present utility in the Post Anesthesia Care Unit, they can incorporated into our system by sealingly affixing them to the patient's face, retaining their connection to the ventilator conduit, and connecting the opposite end to the airator unit as taught and described in these specifications and claims. Preferably, such a mask would be sealingly affixed to the patient's face after surgery by a spray-on adhesive or a tape with an adhesive applied to each side. Others will well appreciate that such masks can be adopted to obtain some of the benefits of our system invention by adding a headstrap thereto.

The Ventilator Circuit

As suggested by this disclosure, any of above described mask alternatives can be integrated into the inventive system of this disclosure. As shown in FIG. 1, that integration includes connection of the ventilator circuit 184 to the conduit connector 56 of the mask 16. This circuit 184 includes a Y connector 185 that communicates with an oxygen supply conduit 186 and with an exhalation conduit 188. While this circuit is preferably the same airway or ventilator circuit that was used in the Operating Room, such can be separately obtained from various sources such as the Hudson Respiratory Care, Inc. of Temecula, Calif. as catalog nos. 1613/690-40 of its 1993-94 catalog. As will be illustrated, the circuit 184 can be connected to the airator 229 of our invention which is located in the PACU.

Transport Problems and Solutions Including the Oxyvent

After surgery, the patient is taken on a gurney to the Post Anesthesia Care Unit, the PACU. However, prior to transport, the patient is disconnected from many of the monitoring devices in the Operating Room (OR) and from the anesthesia machine which had the capabilities of providing oxygen and of positively ventilating the patient. During transport, the patient is normally deprived of a positive supply of oxygen or of ventilation capabilities. Significantly, it is widely known that during this short trip from the OR to the PACU, as many as 30 percent of the patients become hypoxemic (hemoglobin desaturation) due to an insufficient oxygen-air ratio. In addition, some patients may need positive ventilation during this short trip because they are paralyzed or partially paralyzed by neuromuscular blocking agents, have been exposed to high narcotic doses, suffer from lung disease, or been subjected to thoracic surgery.

Figure 13:
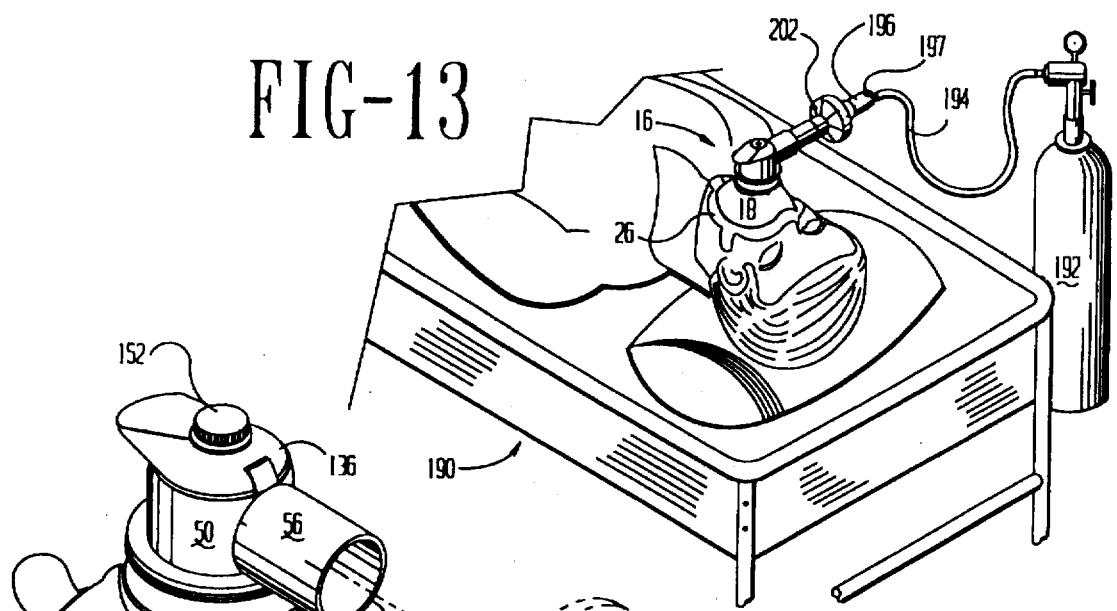
FIG. 13 is a perspective view of a patient on a gurney wearing a mask which is connected to a preferred embodiment of the manually operated "oxyvent" of this invention, the "oxyvent" unit being further connected to an oxygen tank for providing positive pressure ventilation to the patient if needed.
Figure 14:
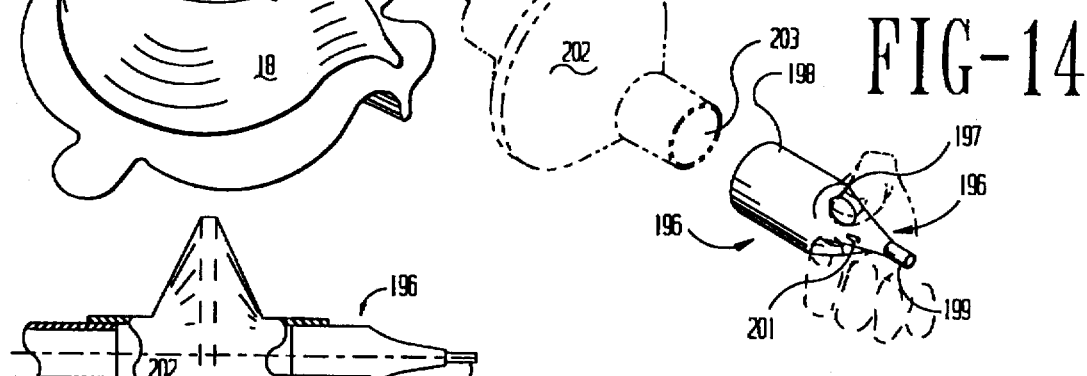
FIG. 14 is an enlarged, exploded view, in perspective, of the mask of FIG. 13 and its connection to the "oxyvent" unit.
Figure 15:
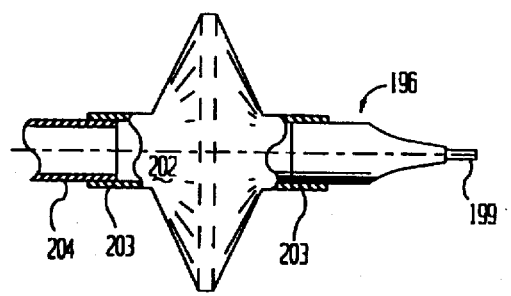
FIG. 15 is an enlarged perspective view of the "oxyvent" unit of FIG. 13 attached to a filter that is sealingly connected to tracheal tube, the "oxyvent" being ready for connection to an oxygen source.

FIGS. 13–15 disclose and depict the use of components of this invention to minimize these problems. In FIG. 13, the patient is positioned on a gurney 190 for transportation from the OR to the PACU. The mask 16 of this invention has been positively adhered to the patient's face by applying pressure to the edge 26 of the mask and compressing the hot melt type adhesive against the patient's skin. An oxygen tank and flowmeter 192 is attached to or physically carried alongside the gurney as a source of oxygen for the patient. Preferably, a standard bacteria filter 202 is also connected to the conduit connector 56 of the mask 16 to preclude pathogen contamination of the atmosphere through the patient's exhalations and coughs. To this filter 202 is connected the unique "oxyvent" component 196 of this invention. This "oxyvent" 196 is a very simple, low cost elongated tubular member 198 with a standard male taper on at least one end which can be inserted into the female tapered tube 203 of the filter 202 (or directly into the mask conduit 56). Preferably, the tubular member 198 has a cone shaped structure at the other end which terminates in a reduced diameter fitting 199 to sealingly mate with a standard oxygen tube 194 that, in turn, connects to the oxygen tank 192. Importantly, the "oxyvent" is provided with two openings 197 which, if desired, can be covered by the physicians' thumb and finger to seal the entire conduit extending from the tank 192 to the patient's mask 16.

During transport of the patient, enriched oxygen is supplied from the tank 192 into the conduit 194. Although some of this oxygen is lost through the openings 197, the patient will, nevertheless, inhale enriched oxygen to minimize the possibility of hemoglobin desaturation and a hypoxemic condition. And even though oxygen is being supplied through the conduit 194, such will have no substantial effect upon the patient's ability to expire through the openings 197 of the "oxyvent" device 196.

In the event that the patient has difficulty respiring during the trip from the OR to the PACU, the nurse or doctor can simply cover the openings 197 with their thumb and finger. Such will forcibly ventilate the patient by directing oxygen, under pressure, to the patient's lungs so as to overcome adverse conditions that may decrement the patient's breathing ability, such conditions including, among other things, neuromuscular blocking agents, high doses of narcotics, lung disease, etc.

FIG. 14 is an enlarged view of FIG. 13 so as to better depict the mask-filter-coupler connections and the application of one's thumb and finger to seal the apertures 197 and forcibly ventilate the patient.

Figure 14A:
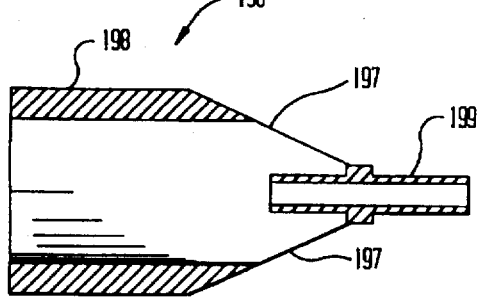
FIG. 14a is a side elevational view of the "oxyvent" unit of our invention.

FIG. 14a is an enlarged sectional view of the "oxyvent" 196 which depicts its tubular structure 197 having a male external fitting 198 and the oxygen fitting at 199. In addition to the control apertures 197 for applying positive pressure to the patient's lungs, the unit can also be provided with a relief orifice 201 which will permit the escape of air and a reduction in the positive pressure applied to the patient should the control apertures 197 be closed too long.

FIG. 15 depicts the application of the "oxyvent" 196 to a tracheal tube 204 of patient. Under some conditions, anesthetists will desire to keep a patient intubated for some time after surgery. Under these circumstances, a filter and "oxyvent" can be connected directly to the tracheal tube during transport so as to provide enriched oxygen and to filter the patient's exhalations. When the patient arrives at the PACU, he can still be connected through the standard ventilator conduits to the airator 229 for scavenging the exhaled anesthesia gases to the outside atmosphere as taught in this specification and depicted in FIG. 1. In summary, the "oxyvent" in the form of the described tubular member of FIGS. 13–15 comprises a very inexpensive tubular oxygenator-ventilator combination.

The Airator

Once the patient arrives at the PACU, he or she can be connected to the airator of this invention. As shown in FIG. 1, such is accomplished by connecting the ventilator circuit 184 to the conduit connector 56 of the mask 16 as shown in FIG. 1. Alternatively, if the patient remains intubated, the ventilator circuit 184 is connected directly to the tracheal tube 204 as shown in FIG. 15. The opposite ends of the ventilator conduits are then connected to the airator invention 229 of this specification as shown in FIG. 1.

The airator 229 is housed in a manifold 230. In substance, the airator comprises a pneumatic circuit having an inspiratory branch 231a and an expiratory branch 231b which perform several important fluid flow control functions reflected in the circuit diagram of FIG. 16. As illustrated, this circuit diagram utilizes the standard symbols of publication Y32.10-1967 of the American National Standards Institute as permitted by the Manual of Patent Examining Procedure, Section 608.02 and 37 CFR § 7.84.

Figure 16:
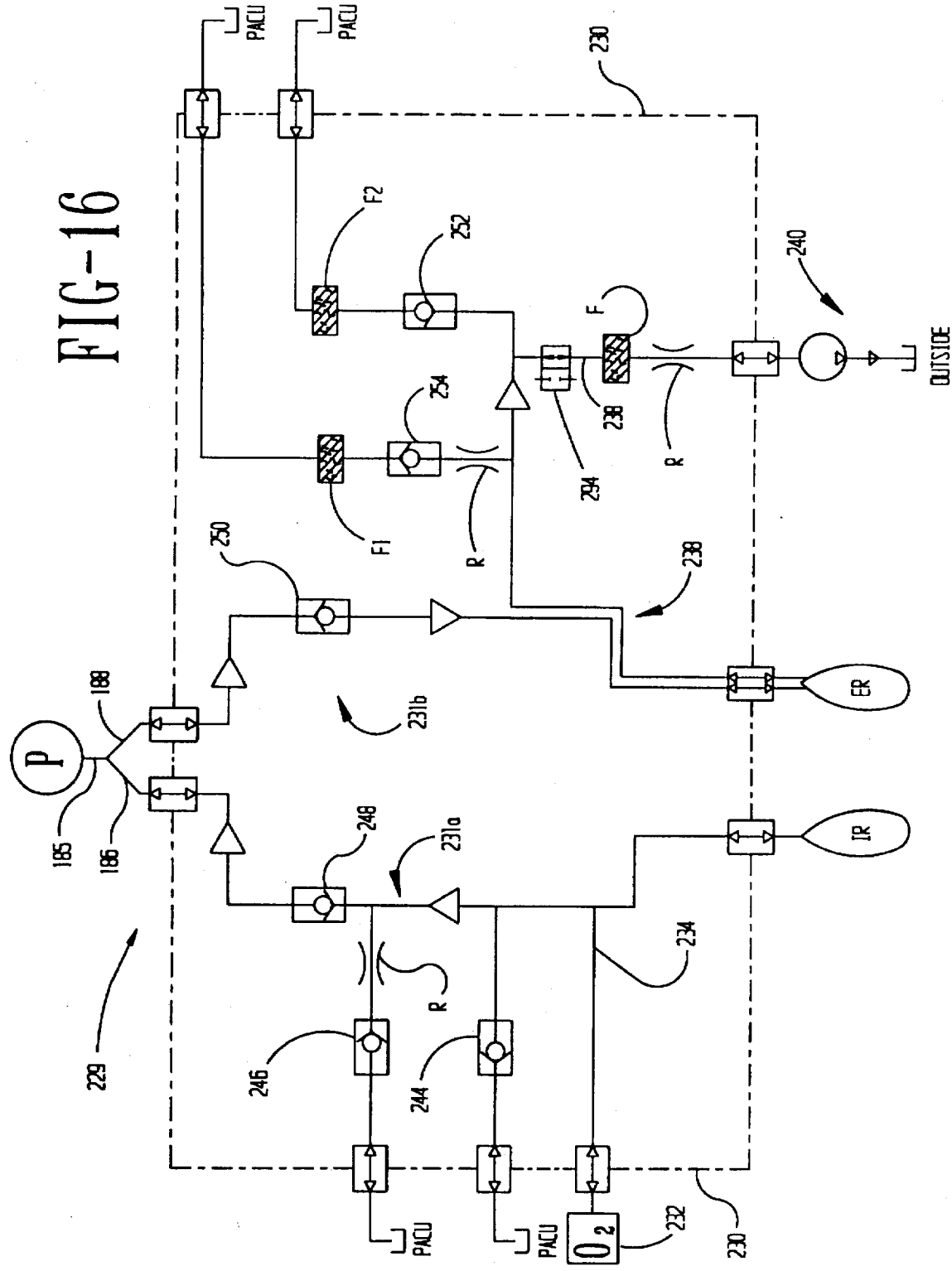
FIG. 16 is a schematic view of the fluid circuit of an airator manifold unit with attached air bag indicators in which the conventional fluid control functions are illustrated by standard symbols.

The inspiratory branch of the pneumatic circuit 231a is connected to the oxygen source 232 through an external conduit 234 as shown in FIGS. 1, 16 and 17. The expiratory branch 231b is connected through an external vacuum conduit 238 to a vacuum pump 240. The remainder of the circuit shown in FIG. 16 is intended to be incorporated inside a housing or shell 230 as shown in FIGS. 1 and 17.

As reflected in FIG. 16, the inspiratory circuit 231a receives oxygen (or an oxygen mixture) under a slight pressure through the conduit 234 and, subject to certain safety valves, delivers the oxygen to the patient P. The safety valves are one-way directional valves 244, 246 and 248. The valve 244 is an inspiratory negative pressure relief valve. This valve opens to permit the patient (P) to obtain air from the PACU atmosphere in the event that the oxygen source 232 is closed or malfunctions. The valve 246 is a positive pressure relief valve that operates in the opposite direction to open the pneumatic circuit to the PACU atmosphere in the event of an air-oxygen over pressure in the circuit 231a between oxygen source 232 and the patient (P). If desired, a restrictor R may be positioned in front of valve 246 to limit oxygen waste to the room atmosphere should an oxygen over-pressure condition occur. The third valve 248 is an inspiratory valve that opens upon the patient's inspirations and closes upon the patient's expirations to force his expirations to the vacuum circuit 231b.

The vacuum or expiratory circuit 231b of the pneumatic circuit 231 is provided with three one-way valves between the patient and the vacuum source 240 that draws the expirations to the OUTSIDE atmosphere. The first valve 250 is a patient expiratory valve that closes as the patient inhales to preclude inhalation of the prior expired air. Another one-way valve 252 is an expiratory positive relief valve that permits the patient to exhale directly to the PACU room atmosphere in the event the vacuum or remainder of the expiratory circuit clogs or closes. The valve 254 is an expiratory negative relief safety valve that permits entry of room air from the PACU into the circuit 131 in the event an excessive vacuum pulled by the vacuum pump 240. A restrictor R may be placed between this negative pressure relief valve 254 and the vacuum source 240 to limit magnitude of the PACU room air that is pumped to the OUTSIDE atmosphere as depicted in FIG. 16.

Preferably, the airator 229 and its expiratory circuit 231b also includes another restrictor R which limits the demand on the vacuum source 240 to a flow rate just above the normal exhalation flow rate of a patient. Such will help to limit the demand on the vacuum system of the hospital facility that might otherwise occur from the installation of several of these scavenging units. To insure that the restricted orifice R does not become clogged by a patient's exhalations, a filter F may be placed just upstream of the orifice R. Finally, a manually operated shutoff valve 294 controls access of the circuit 231b to the vacuum source. Alternatively, this shutoff valve may take the shape of a variable flow control valve that uses, for instance, an eccentric plug to variably close the conduit. Preferably, this shutoff valve 294 is physically mounted on the airator housing or shell as shown in FIG. 1.

In addition to the filter F that may be installed to protect the orifice R from clogging, an additional filter may be installed to preclude the passage of bacteria from the patient (P) to room atmosphere. This filter is F2 positioned as depicted in FIG. 16. It may be a HEPA filter (High Efficiency Particulate Air filters) which is conventionally available, or alternatively, it may be formed integrally as part of the airator shell 230. Also, filter F1 may be provided to filter dust and particulate matter if room air enters the airator through the negative pressure relief valve 254.

Finally, the airator manifold circuit may also include an inspiratory reservoir bag (IR) and an expiratory reservoir bag (ER) to permit a visual indication of the operation of the system and the breathing of the patient.

Those skilled in the art will appreciate that there are numerous ways of incorporating the pneumatic circuit 231 of this invention into an airator housing or manifold 230. In large part, such will depend upon the preferences of the manufacturer. For example, the circuit 231 might be formed of conduits and fittings for receiving the one-way valves, filters, restrictors, etc. which are then installed in a separately formed housing or shell 230. Alternatively, the circuit 231 can be integrally molded into housing by a plastic molding facility. Under this alternative, fittings could be formed for receiving the external conduits, the filters, one-way valves, etc. In addition to incoporating the pneumatic circuits of this invention, the shell 230 may also be provided with clear, transparent windows W to permit the hospital staff to visually observe the functioning of the six one-way valves of the circuit.

If the circuit 231 is integrally molded in a housing, each of the one-way check valves may take the form of a flat disk which seats on an annular valve seat projection positioned within a molded conduit of the airator unit. Such disks are conventional to anesthesia gas equipment. They are normally formed of a ceramic or mica material and maybe obtained from the ceramic group of Coors Ceramics Company, Golden, Colo. Alternatively, such one-way valves may take the form of balls that are mounted to seal into a funnel shaped valve seat. Those skilled in the art will appreciate that the size and weight of the valves may vary depending, in part, upon the size of the conduits and the position of the components within the housing. Such will have some effect on the pressure and velocity heads, the forces and work needed to open the valves.

The preferred embodiment of the airator circuit 231 is incorporated into a molded housing such as that depicted in FIG. 17. As shown in FIGS. 17 and 18, a principal component of the airator circuit is the one way valves 244–254. They are uniquely formed and molded of a hard plastic such as the Lexan® 123R polycarbonate mentioned earlier. Each is initially formed from three parts which include a base 270, a disk 282 and a retainer 284 as depicted in FIG. 18. The base 270 includes a base plate 272 having an aperture 274 extending therethrough with a raised valve seat 273 extending about the circumference of the aperture. Positioned about the outer edge of the plate 272 are vertical posts 276 having a reduced end diameter as illustrated. The disk 282 is a flat disk that will mate with and sealingly seat upon the valve seat 273 to substantially preclude air flow between them in the closed position. The retainer 284 is provided a central opening 285 having a diameter less than that of disk 282 and a plurality of apertures (unnumbered) that will extend over the reduced diameter of the posts 276.

In assembling the one-way valves, the disk 282 in inserted within the posts 276 and upon the valve seat 273. Then, the retainer ring 284 is positioned on the posts 276 such that their reduced end diameters extend through the small apertures in retainer ring 284. Thereafter, the reduced diameter posts are sonically welded to the retainer plates in the conventional manner to define a unitary one way valve with a captured disk 282.

Valves formed of polycarbonate can be molded with sufficient flatness to provide excellent sealing capabilities in this environment. They are also extremely durable and resist wear. Importantly, such valves are also of a very light weight and require a very low force and work expenditure to open and close them. Importantly, the molding of these valves eliminates the machining of valve seats of stainless steel and their complicated assembly as is done in present day expensive anesthesia machines used in the OR.

To further minimize costs and simplify assembly, the base of relief valves 244–254 is also provided with a lower flange 280 that, together with the base 272 defines a groove or slot 278 that is received in a sealing relationship in the airator housing 230.

Preferably, the airator housing 230 is also molded of a polycarbonate plastic in the shape depicted in FIGS. 17, 19 and 20. This shape includes a housing with molded webs or lands 286 to define passages of the pneumatic circuit 231 and its components 231a and 231b. As shown in FIG. 19, these webs or lands are also provided with U-shaped recesses 288 that will receive the groove or slot 278 of the relief valves 244–254.

In FIG. 17, the inspiratory circuit 231a is depicted on the left side of the housing 230. This circuit receives oxygen from a conduit connected to oxygen source or port 232 and delivers it to the patient inspiratory port IP through the inspiratory one way valve 248. In the event that the oxygen source is clogged or fails to open, the patient can draw air from the PACU environment through the open slots 243 and the negative pressure relief valve 244 which opens as soon as the patients attempts to inhale in the absence of an enriched oxygen supply. Alternatively, if the oxygen source 232 provides too much pressure, the positive pressure relief valve 246 will open to permit the excess oxygen pressure to vent to the PACU atmosphere through the elongated slots 285 on the back of the housing 230.

The expiratory circuit 231b is molded on the right side of the airator housing 230. Again, webs or lands 286 in conjunction with the housing walls define the passages of this circuit. The patient exhales into the expiratory port labeled EP and his expiration opens the patient expiratory valve 250 to travel down to the expiratory bag and then upward as shown by the arrows toward the vacuum port 240. As more clearly illustrated in FIGS. 19 and 20, the expiration normally tracks the arrows in the channel 231b and passes into an opening or filter chamber 290 behind a plate 292. If the vacuum control knob 294 is open so that its recess 296 is aligned with the restricted orifice R in the plate 292, the patient's expiration is drawn to the vacuum port 240 within chamber 242. The filter F within chamber 290 (FIG. 20) will trap and preclude expiratory moisture or sputum from clogging the restricted orifice R. Alternatively, if the vacuum is clogged or its port unopened, the patient's expiration will open the expiratory positive pressure relief valve 252 (FIG. 18) and pass through to the PACU. If desired, a filter $F_2$ may filter the expiratory air as it passes into the PACU environment. Alternatively, if the vacuum 240 is excessive, the expiratory negative pressure relief valve 254 will open to draw PACU air into the housing 230 through the filter $F_1$ rather than exposing the patient to such a negative pressure and increasing his breathing effort.

In manufacture and assembly, the U-shaped recesses 288 of the web 286 of FIG. 19 are coated with an epoxy (not shown) for adhesively receiving the groove or slot 278 of the one way valves in sealing relationship. Then, the front edge of the webs 286 and of the one way valves 244–254 are flush and in the same plane so that an epoxy can be applied thereto for sealing engagement with the front panel 300 of FIG. 19. (However, the front edge of the web section 291 is recessed to permit the patient's expiration to flow behind the plate 292 and then forward through the aperture uncovered by the vacuum control knob as depicted in FIG. 19.) After the epoxy is applied to the edges of the web sections and the front edge of valve bases 272, the front cover 300 is placed over the housing 230. Importantly, the back side (not shown) of the front cover 300 is also provided with webs or lands 302 that mate with the webs 286 of the housing 230 to fully define the conduits and chambers within the airator. (Only some of the lands 302 are illustrated by dotted lines, but those skilled in the art will immediately appreciate the total number, thickness and length of all of the lands that will be needed). Significantly, the epoxy acts, not only to bond the front cover 300 to the housing 230, it also provides a separate seal for each conduit and chamber within the housing. An O-ring seal is inserted between the vacuum control knob 294 and the front panel 300 as shown in FIG. 20.

FIGS. 16 and 17 also disclose that the expiratory circuit 131b forces the patient's exhalations downward into close proximity with the expiratory bag ER and then upwardly for a relatively substantial distance to the vacuum 240. This positioning of these components helps to assure that moisture and other particles of the patient's expirations drop into the ER bag and do not ascend to clog the restrictors R.

In use, the airator housing 230 may be wall mounted adjacent the oxygen source 232. Preferably, however, and as shown in FIG. 1, the airator housing 230 is mounted on a portable stand 265. This stand includes a telescopic member 266 which can be reciprocated within tubular column 268 for such vertical adjustments as may be necessitated by the height of the patient's bed. In additional to vertical adjustment, the stand is portably supported by a conventional, lightweight base (not shown).

At the top of the telescopic member 266 (FIG. 21a) is a releasable mounting bracket 310 for mounting the airator housing 230. This bracket has a cylindrical collar 312 which extends over the top of the telescopic member 266. The top of the collar 312 is closed by a flat supporting surface 314. Underneath this flat supporting surface are four supporting longitudinal webs 316–322 which resist bending of the flat surface 314. During assembly, two of these webs, 318 and 320, are inserted into two slots 324 of an opening 325 of the airator housing 230. These slots 324 guide the bracket into the housing 230. The outside webs, 316 and 322 also engage the opposite end walls 326 of the opening 325. The end walls 326 are tapered in their vertical dimension to mate with the vertical taper of webs 316 and 322 of the bracket 310. The taper of these webs and end walls result in a wedging contact which provides substantial rigidity and stability to the interconnection between the housing 230 and the bracket 310.

The bracket 310 has a center locking tongue 330 and detent tab 332 that are extended completely through the opening 325. The detent tab 332 even extends through a small opening (unnumbered) of the front cover 300 and engages the upper edge of that opening to lock the airator housing 230 onto the stand 265. (See FIG. 17).

Method of Use

The preferred use of our invention begins in the Operating Room. After surgery, the anesthetist will normally disconnect the patient from the anesthesia machine by disconnecting the airway circuit from the cuffed tracheal tube inserted into the patient's trachea. Thereafter, the mask 16 of this invention is applied to the patient's face. In light of the cavity construction of this mask, it may be applied directly over the tracheal tube which may be temporarily left in place. Alternatively, the tracheal tube may be removed by the anesthetist before the mask is applied. Thereafter, the patient is moved to the Post Anesthesia Care Unit with the airway conduit that was used in the OR.

During this transport and as shown in FIG. 13, the patient is preferably connected to an oxygen tank 192 via a conduit 194, the "oxyvent" 196 of this specification, a bacteria filter 202 and the mask 16 of this invention. Such transport will, in our view, substantially reduce the number of patients who become hypoxemic for lack of oxygen by providing them with enriched oxygen from the tank. In addition, the oxyvent can be use to pressure ventilate a patient by simplisticly closing the exhaust openings 197 momentarily and repeatedly in rhythm with the patient's normal rate of breathing. Finally, the use of the bacteria filter will substantially reduce the possibility of expiration of pathogens in the atmosphere during the transport.

Alternatively, if the patient remains intubated, the patient can still be connected to the oxygen tank via a bacteria filter, the "oxyvent" and a conduit. Similarly, the foregoing advantages are also available to the intubated patient. These concepts and benefits are summarily depicted in FIGS. 13–15 of the attached drawings.

Upon arrival at the Post Anesthesia Care Unit, the airway or ventilator circuit 184 is interconnected between the patient's mask 16 and the airator 229 as shown in FIG. 1. Simultaneously, the nurse insures that the oxygen valve is on, that oxygen or an oxygen mixture is flowing to the patient, and that the vacuum is pulling a suction. Visual observation of the IR and ER respiratory bags and the flowmeter FM as well as visual inspection of the one way valves through the windows of the airator 229 will assure that the patient's respiratory functions are proper and that the patient's contaminated expirations are removed to the outside atmosphere. In the event that the patient remains intubated, the same benefits can be achieved by connecting the ventilator conduits directly to the tracheal tube, or alternatively, affixing the mask over the tube and connecting the ventilator conduits to the connector 56 of the mask 16.

As demonstrated, the patients in the PACU benefit from the system by receiving a controlled air-oxygen ratio through the apparatus, system and methods of this invention. In addition, the stress of the PACU upon the hospital staff is reduced because, visually and from a distance, the staff can visually determine that a patient is breathing normally. Simultaneously, the hospital staff and the patients are protected from the ill effects of expired anesthesia gases and airborne pathogens that, otherwise, would remain in the PACU rather than being scavenged to the outside atmosphere. Hopefully, the fear of a patient's cough in the staff's face will be substantially eliminated by the use of the suction port in the mask. Similarly, the fear of headaches, and reduced dexterity, spontaneous abortions, neurological and other diseases will be eliminated from the PACU by the inventions disclosed herein.

Figure 22:
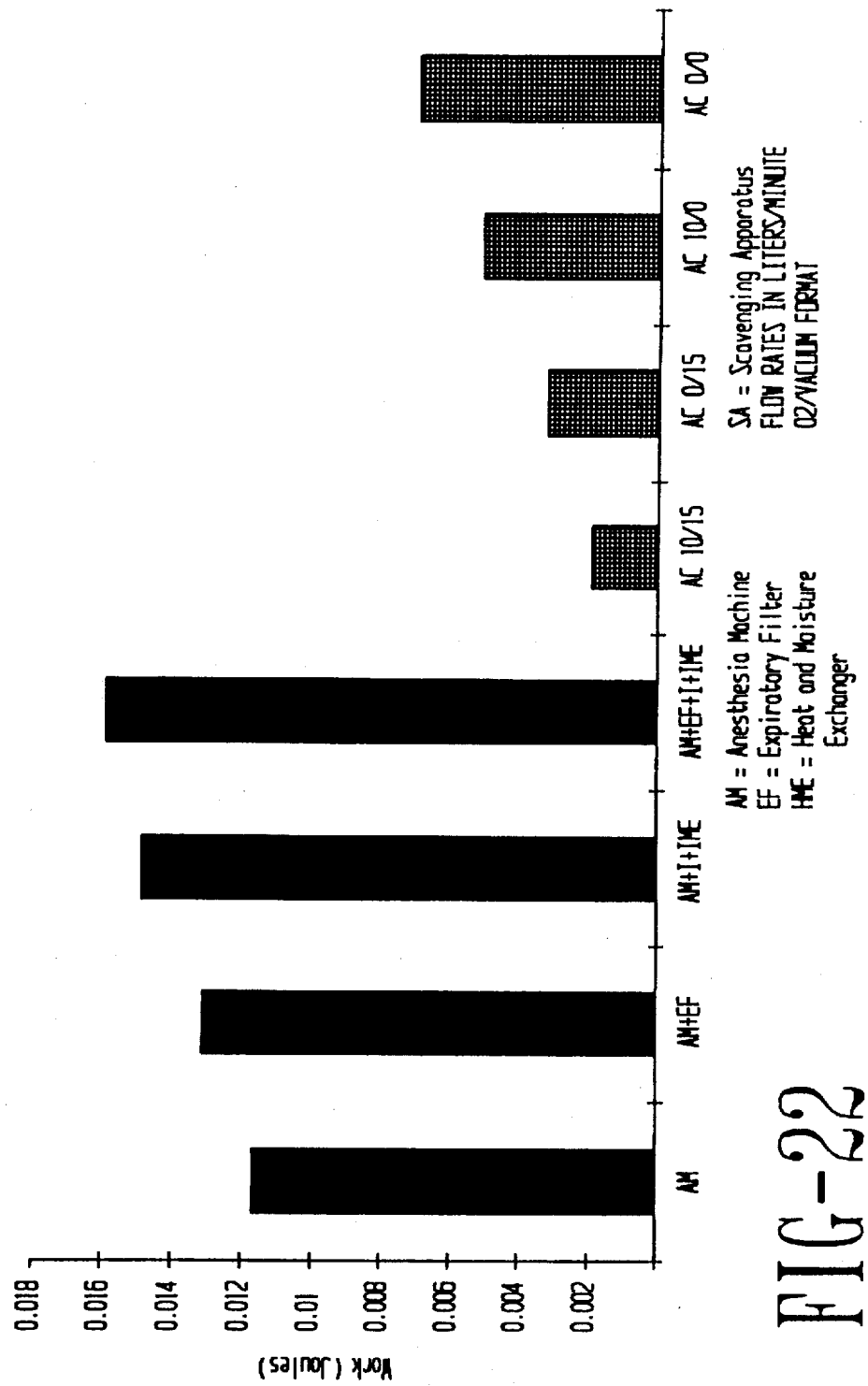
FIG. 22 is an a graph reflecting the work, in joules, required by a patient to ventilate through this invention compared to anesthesia machines.

Significantly, the use of the scavenging system of this invention will have no adverse effect upon the patient's breathing. Indeed, the effort and work required to breath through the scavenging apparatus disclosed herein will be substantially less than the work required to breathe through the standard anesthesia machine, their filters and heat and moisture exchangers. Such is true even if the hospital staff failed to open or turn on both the oxygen source and the vacuum source. Indeed under these latter circumstances, the breathing work required of a patient breathing through our scavenging apparatus (SA) would be substantially less than that required by the anesthesia machine (AM). (A comparison is depicted in FIG. 22).

MODIFICATIONS

Those skilled in the art will find that, in part, the inventions depicted herein will have directly applicability in other areas of the health care institutions. For example, the apparatus will serve as an alternative, low cost inhalation therapy device in which a drug such as ribavirin may be administered through the airator, ventilator conduits and mask to the patient with his expirations being scavenged directly to the vacuum port connected to the outside atmosphere. In addition, the entire apparatus will have application in bronchoscopy suites so as to permit the physician to administer anesthesia through the airator and mask to the patient while simultaneously inserting examination devices through the sealable aperture 82 of membrane 80 (see FIG. 4). The use of this apparatus in connection with bronschoscopies will protect the physician from pathogens and anesthesia gases by simultaneously scavenging the patient's expiration through the airator to the vacuum port and to the outside atmosphere. In additional, the apparatus will have application in emergency rooms for use with patients suspected of having tuberculosis. Similarly, the various components of this apparatus will provide benefits such as positive pressure ventilation during patient transport.

Moreover, this disclosure will suggest to those skilled in the art modifications of the apparatus, systems and manufacturing methods that can be made to the disclosure for achieving the numerous benefits without any substantial departure from the teachings of this disclosure. For example, the mask base 18 can be injection molded, thermoformed, or merely stamped from pliable thermoplastic film. Similarly, different adhesives can be used to seal the mask to the patient's face—and such can be used through a backing tape medium or applied directly to mask base 18 or a standard anesthesia face mask with a pillow. In addition, windows W can be formed in the airator face as depicted in FIG. 1 so that proper operation of each of the one-way valves can be observed and assured. Visual operation of these valves, together with the visual observation of the flow and the respirator bags, will assist the hospital staff in observation and evaluation of each patient's condition. Significantly, the pneumatic circuit of this invention can take many forms— forms that may extend from a low cost conduit and valve assembly to an molded housing requiring expensive molds. In use, persons skilled in the art will find that the mask of this invention, with or without the modifications of FIGS. 12, 12a and 12b can be used as an anesthesia mask. Alternatively, many benefits of our apparatus method can be achieved by using the conventional anesthesia mask or other masks in conjunction with the airator of this disclosure and with the methods that are taught and suggested to persons of skill in the art.

We claim:

1. A post anesthesia patient care apparatus for providing oxygen to a patient and for precluding contamination of the atmosphere of a post anesthesia care facility by a patient's expirations of anesthesia gases or pathogens, said patient care apparatus comprising:
   a) a generally transparent face mask having a mask base with a pliable outer edge carrying an adhesive for sealingly engaging the patient's face to preclude leakage of gas from between a patient's face and the outer edge of the mask base into the atmosphere, said mask base extending from said outer pliable edge toward a generally central opening to be positioned approximately above a patient's mouth, said central opening including a seal-interlock component for sealingly receiving a cover adapter;
   b) a generally transparent cover adapter carrying a mating seal-interlock component for sealingly mating with the seal component of said mask base, said cover adapter having a connector for connecting said mask to a ventilator circuit;
   c) said mask including a quick disconnect device for removing at least a portion of said mask for quick access to a patient's mouth or nasal passages;
   d) a ventilator circuit removably and sealingly connected to said connector of said cover adapter, said circuit including a first conduit for delivering oxygen to a patient and a second conduit for receiving a patient's expirations; and
   e) an airator having a pneumatic circuit with a first inspiratory branch interconnected between an oxygen source and the first conduit for delivering the oxygen mixture to a patient, and a second expiratory branch interconnected between second conduit and a vacuum source for transmitting patient expirations, including contaminants, outside the patient's atmosphere within a post anesthesia care facility.

2. A post anesthesia patient care apparatus as set forth in claim 1 in which
   a) the adhesive is a pressure sensitive adhesive directly applied to the pliable outer edge of the mask.

3. A post anesthesia patient care apparatus as set forth in claim 1 in which
   a) the adhesive comprises a foam adhesive bead having a sufficient cross sectional thickness as to compressingly engage and seal to a patient's face.

4. A post anesthesia patient care apparatus as recited in claim 3 in which said foam adhesive is provided with a release strip backing to protect the adhesive until use.

5. A post anesthesia patient care apparatus as set forth in claim 1 in which said quick disconnect device of said face mask comprises a detent mechanism between said releasable seal interlock components for quickly disconnecting said adapter from the base and exposing the patient's face.

6. A post anesthesia patient care apparatus as set forth in claim 1 in which said cover adapter includes:
   a) an opening for permitting insertion of a medical device into the patient's mouth without removing said mask;
   b) a flexible access cover for said opening formed of an elastic-stretchable material and having a small aperture there in for sealingly receiving a medical instrument; and
   c) a removable cover cap normally positioned to extend over said flexible cover for sealing the interior of said mask, but removable when necessary to insert a medical device such as a suction catheter into a patient's mouth.

7. A post anesthesia patient care apparatus as set forth in claim 1 in which the inspiratory branch and the expiratory branch of the airator are provided with inflatable bags to permit visual observation of a patient's ventilation status and with a negative pressure relief valve to insure proper ventilation for a patient.

8. A post anesthesia patient care apparatus as recited in claim 1 in which said airator is supported by a releasable mounting bracket to facilitate replacement thereof.

9. A post anesthesia patient care apparatus for protecting a patient's environment from contamination by a patient's exhalations of contaminants such as anesthesia gases or pathogens and for providing a patient with a controlled oxygen mixture for inhalation, said apparatus comprising:
   a) a face mask formed of a generally transparent material having a base with an outer pliable surface for sealingly engaging a patient's face to minimize leakage of gas from between the patient's face and the outer pliable surface of the face mask, said base extending from said outer pliable surface towards a central cavity covering the patient's mouth and nose and terminating in a coupler for sealingly coupling said mask to a ventilator circuit;
   b) a ventilator circuit sealingly connected to said coupler of said mask and to an airator pneumatic circuit for transmitting inhalation and exhalation gases between the patient and the airator pneumatic circuit; and
   c) an airator pneumatic circuit sealingly coupled to the ventilator circuit, said airator circuit including an inhalation circuit for connection with an oxygen mixture source and having at least one pressure relief valve permitting gas flow to the patient upon demand and an exhalation circuit connected to a vacuum source for transmitting a patient's exhalations out of a patient's environment, said exhalation circuit having at least one pressure relief for limiting the vacuum that is applied to the exhalation circuit.

10. A post anesthesia patient care apparatus as recited in claim 9 in which said airator circuit is contained in a housing, and
    a) said housing is provided with ports for facilitating connection to an oxygen mixture source, a patient and a vacuum source for facilitating proper ventilation of a patient, and
    b) said housing and said circuits are provided with visual aid devices to facilitate observation of a patient's breathing status.

11. A post anesthesia patient care apparatus as recited in claim 9 in which
    a) said face mask includes a quick detach device for permitting quick access to a patient's mouth, and
    b) said quick detach device comprises a seal interlock device releasably interconnecting said coupler and said mask.

12. A post anesthesia patient care apparatus as recited in claim 9 in which
    a) said outer pliable surface of said base is connected to said base by a hinge of a reduced cross sectional thickness to facilitate conformity and sealing engagement with the patient's face, and
    b) said surface carries an adhesive for sealingly engaging the patient's face.

13. A post anesthesia patient care apparatus as recited in claim 9 in which said coupler of said face mask is also provided with a capped opening for facilitating the insertion of a suction catheter into the patient's mouth for suctioning excess fluids therefrom, said aperture including a flexible access cover with an aperture therein for sealingly receiving said catheter and for preventing the escape of a patient's exhalations from about said catheter.

14. A post anesthesia patient care apparatus as recited in claim 9 in which said outer pliable surface carries a compressible foam adhesive for sealing engagement with a patient's face.

15. A post anesthesia patient care apparatus as recited in claim 9 in which said mask coupler and said airator pneumatic circuits have standard ports for connection to the industry standard ventilator conduits for reducing the costs of using such an apparatus.

16. A post anesthesia patient care and scavenging apparatus, said apparatus comprising:
   a) an airator connected to an enriched source of oxygen and a vacuum within a post anesthesia care area of a health care facility, said airator having couplings for connection to ventilation inspiratory and expiratory conduits;
   b) said airator having an inspiratory pneumatic circuit interconnected between said enriched oxygen source and said inspiratory conduit and having at least one directional flow control valve therein for permitting flow from a post anesthesia care area to the inspiratory circuit in the event of a negative pressure therein;
   c) said airator having an expiratory pneumatic circuit interconnected between said expiratory conduit and said vacuum, said expiratory circuit having at least one directional flow control valve therein for permitting flow from a post anesthesia care area to the expiratory circuit in the event of an excess negative pressure created by the vacuum;
   d) a patient mask sealingly engaged to the patient's face and adapted to be coupled to said ventilation conduits for delivering an enriched oxygen mixture to the patient and for delivering his expirations to the vacuum.

17. A post anesthesia patient care and scavenging apparatus as recited in claim 16 in which said mask has a quick disconnect device for quickly removing at least a portion of said mask and permitting immediate access to a patient's mouth.

18. A post anesthesia patient care and scavenging apparatus as recited in claim 17 in which said quick disconnect device comprises a removable coupler that is sealingly and removably affixed to said mask so as to permit immediate removal thereof.

19. A post anesthesia patient care and scavenging apparatus as recited in claim 16 in which said mask is provided with a flexible suction aperture for permitting sealing access of a suction catheter into the patient's mouth.

20. A three piece patient care mask, said mask comprising:
   a) a base having a generally annular pliable, gas impervious edge for circumscribing a patient's mouth and nose and extending to a central opening generally above the patient's mouth;
   b) an annular insert member sealingly molded and fixed within said central opening for receiving an adapter and for adding stiffness to said pliable base;
   c) a closure adapter sealingly mounted within said insert, said adapter having a conduit connection for coupling said mask to a ventilator circuit for delivering an oxygen mixture to said patient and for scavenging the patient's exhalations to the atmosphere;
   d) a quick detachable physical interlock between said insert member and said adapter for precluding their inadvertent separation and for permitting immediate access to the patient's mouth; and
   e) at least one seal interposed in said central opening between the base and the adapter to preclude the loss of gases from between the base and the adapter.

21. A patient care mask as recited in claim 20 in which said base is provided with extension taps to facilitate the removal of the entire mask from a patient's face.

22. A patient care mask as recited in claim 20 in which said seal is a radial type lip seal.

23. A patient care mask as recited in claim 20 in which said physical interlock comprises a resilient bayonet detent locking mechanism.

24. A patient care mask as set forth in claim 20 in which an adhesive is provided around the impervious edge of the base circumscribing a patient's mouth.

25. A patient care mask as set forth in claim 24 in which the adhesive comprises a foam adhesive bead.

26. A post anesthesia patient care mask for preventing contamination of a hospital facility of anesthetic gases or pathogens, said mask comprising:
   a) a base formed of a gas impervious material, said base having a pliable circumferential edge carrying an adhesive for sealingly engaging a patient's face;
   b) said base having a coupler defining a central cavity adapted to extend over a patient's nose and mouth and having a connector for coupling said mask to a ventilator circuit for transmitting an oxygen mixture to the patient and for scavenging the patient's exhalations to the atmosphere;
   c) said coupler also having an access opening covered by a flexible, stretchable cover and a removable cap for permitting sealed insertion of a medical instrument through said cover and said access opening.

27. A post anesthesia patient care mask as recited in claim 26 in which said coupler is a quick detachable device sealingly and removably joined to said base.

28. A post anesthesia patient care mask as recited in claim 26 in which said mask carries at least one accessible pull tab that is free of adhesive for breaking the adhesive seal to the patient's face and for removing said mask in an emergency.

29. A post anesthesia patient care mask as set forth in claim 26 in which
   a) the adhesive is a hot melt adhesive; and
   b) said adhesive has a protective backing strip applied thereto prior to use.

30. A post anesthesia patient care mask as set forth in claim 26 in which the adhesive comprises a compressible foam adhesive bead for facilitating sealing engagement with the patient's face.

31. A patient care mask for sealingly engaging a patient's face, said mask comprising:
   a) a base formed of a clear, gas impervious material joined to a central cavity adapted to extend over a patient's nose and mouth and to couple to a ventilator circuit for transmitting an oxygen mixture to the patient and for scavenging the patient's exhalations to the atmosphere;
   b) said base having an outer edge for conforming to the patient's face; and
   c) a compressible cellular foamed adhesive defining a foam bead extending around the outer edge for sealingly engaging said outer edge and said mask to said patient.

32. A post anesthesia patient care airator apparatus for providing oxygen to a patient and for precluding contamination of a patient's environment within a health care facility by a patient's expirations of contaminants such as anesthesia gases and pathogens, said apparatus comprising:
   a) a small portable housing with an oxygen port for receiving an oxygen-gas mixture, a patient inhalation port for delivering an oxygen-gas supply to a patient, and an expiration port for receiving a patient's exhalations and a vacuum port for connection to a vacuum source;

b) an inspiratory circuit within said housing interconnecting the oxygen port with the patient inhalation port, and an expiratory circuit interconnecting the patient expiration port with the vacuum port;

c) said inspiratory circuit having a one-way valve for permitting oxygen to flow to the patient from the oxygen port and for precluding reverse flow, and a negative pressure relief valve for permitting the patient to breathe from the atmosphere of the facility in the event the oxygen supply is closed or malfunctions; and d) said expiratory circuit having a one way valve for preventing patient rebreathing of his expiration, a positive pressure relief valve permitting the patient's to expiration to exhaust to the atmosphere in the event of clogging of the vacuum source, and a negative pressure relief valve for permitting air to be drawn into the expiration circuit in the event excessive negative pressure is imposed on the expiration circuit;

e) said inhalation circuit being provided with a visible inspiratory reservoir bag; and f) said exhalation circuit being provided with a visible expiratory reservoir bag.

33. A post anesthesia patient care airator apparatus as recited in claim 32 in which at least one of said valves comprise:

a) a base formed of a molded polycarbonate material, said base having an opening circumscribed by a raised disk valve seat and support structure for a retainer;

b) a light weight flat disk formed of a molded polycarbonate material adapted to sealingly engage said disk valve seat;

c) a retainer mounted on said support structure for retaining said disk above said seat and d) said base having a positioning-retaining flange for facilitating assembly of said control valve within said circuits.

34. A low cost, post surgery apparatus for supplying an oxygen-gas mixture to a patient and for scavenging a patient's expiration, said apparatus comprising:

a) a housing with an oxygen port for receiving an oxygen-gas mixture and an exhaust port for connection to a vacuum;

b) an inspiratory circuit within said housing interconnecting the oxygen port with a patient for providing an oxygen mixture to a patient, and an expiratory circuit interconnecting a patient with the exhaust port for scavenging his exhalations out of the patient's health care area;

c) visual indicator devices interconnected to at least one of said circuits for providing a visual indicator of the patients ventilation status;

d) a mounting device for supporting said housing; and e) a mounting mechanism removably interconnecting said airator housing with said mounting device and for facilitating replacement.

35. An airator apparatus as recited in claim 34 in which a) said expiratory circuit is provided with a negative pressure relief valve to limit negative pressure generated in said expiratory circuit by said vacuum;

b) said expiratory circuit is also provided with provided with a positive pressure relief valve to permit the patient's expiration to the atmosphere in the event of a vacuum malfunction.

36. A method of providing post anesthesia health care to a patient and for precluding contamination of a post anesthesia health care facility by patient expirations of anesthetic gases, said method comprising the steps of:

a) applying a gas impervious mask in sealing engagement to a patient's face, said mask having a coupler for connection to a inspiratory and expiratory conduits;

b) connecting said mask and its coupler to an inspiratory circuit and delivering a controlled oxygen mixture to the patient;

c) connecting said mask and its coupler to an expiratory conduit and scavenging the patient's expirations to the outside atmosphere via a vacuum source;

d) connecting said inspiratory and expiratory conduits to visual indicators for providing a visual observation of the patient's respiratory function.

37. A post anesthesia patient care apparatus for providing enriched oxygen to the patient to prevent hemoglobin desaturation and for positively ventilating a patient who has difficulty breathing as a result of conditions such as anesthesia agents, neuromuscular blocking agents, high doses of narcotics, lung disease, etc, said post anesthesia apparatus comprising:

a) a face mask formed of a generally transparent material having a base with an outer pliable surface for sealingly engaging the patient's face to minimize leakage of gas from between the patient's face and the outer surface of the face mask, said base extending from said outer surface towards a central cavity covering the patient's mouth and nose and terminating in a coupler conduit;

b) an oxyvent device comprising a generally tubular member having a first sealed interconnection with said coupler, and adapted to have a second sealed connection with an oxygen source, said oxyvent device having at least one aperture open to the atmosphere, said aperture being manually closable to apply intermittent positive pressure from the oxygen source to the patient to preclude oxygen desaturation.

38. A post anesthesia patient care apparatus as recited in claim 37 in which a) said face mask includes a quick detach device for permitting quick access to a patient's mouth and nasal passages, and b) said quick detach device comprises a release detent for disconnecting said coupler from said mask.

39. A post anesthesia patient care apparatus as recited in claim 37 in which said oxyvent device is provided with a relief orifice for preventing the application of excess pressure to the patient.

40. A low cost, oxyvent device for providing enriched oxygen to a patient to prevent hemoglobin desaturation and for positively and intermittently ventilating a patient who has difficulty breathing as a result of conditions such as anesthesia agents, neuromuscular blocking agents, high doses of narcotics, lung disease, etc., said oxyvent comprising:

a) a tubular conduit adapted to be interconnected between a patient and an oxygen pressure source;

b) two aperture in said conduit for permitting the patient to exhale without restriction, said apertures being momentarily closable by the application of a person's thumb and finger to said apertures to forcibly ventilate a patient.

* * * * *